(12) United States Patent (10) Patent No.: US 11,432,748 B2
Abul-Haj et al. (45) Date of Patent: Sep. 6, 2022

(54) COMMON DEPTH NONINVASIVE GLUCOSE CONCENTRATION DETERMINATION ANALYZER APPARATUS AND METHOD OF USE THEREOF

(71) Applicants: Roxanne Abul-Haj, Sedona, AZ (US); Kevin Hazen, Flagstaff, AZ (US); Christopher Slawinski, Mesa, AZ (US); Benjamin Mbouombouo, Saratoga, CA (US); Alodeep Sanyal, San Jose, CA (US); Alan Abul-Haj, Sedona, AZ (US)

(72) Inventors: Roxanne Abul-Haj, Sedona, AZ (US); Kevin Hazen, Flagstaff, AZ (US); Christopher Slawinski, Mesa, AZ (US); Benjamin Mbouombouo, Saratoga, CA (US); Alodeep Sanyal, San Jose, CA (US); Alan Abul-Haj, Sedona, AZ (US)

(*) Notice: Subject to any disclaimer, the term of this patent is extended or adjusted under 35 U.S.C. 154(b) by 433 days.

(21) Appl. No.: 16/777,832

(22) Filed: Jan. 30, 2020

(65) Prior Publication Data

US 2020/0337612 A1 Oct. 29, 2020

Related U.S. Application Data

(63) Continuation-in-part of application No. 16/691,611, filed on Nov. 22, 2019, and a continuation-in-part of
(Continued)

(51) Int. Cl.
*A61B 5/145* (2006.01)
*G01J 3/10* (2006.01)
(Continued)

(52) U.S. Cl.
CPC ........ *A61B 5/14532* (2013.01); *A61B 5/0022* (2013.01); *A61B 5/0059* (2013.01);
(Continued)

(58) Field of Classification Search
CPC . A61B 5/14532; A61B 5/0022; A61B 5/1455; A61B 5/0059; A61B 5/6832; G01J 2003/102
See application file for complete search history.

(56) References Cited

U.S. PATENT DOCUMENTS

2014/0024904 A1* 1/2014 Takinami ............. A61B 5/1455 600/316
2016/0354015 A1* 12/2016 Zhang .................. A61B 5/0075

* cited by examiner

*Primary Examiner* — Ted M Wang
(74) *Attorney, Agent, or Firm* — Kevin Hazen

(57) ABSTRACT

The invention comprises a method and apparatus for sampling optical pathways having a common tissue depth, such as a maximum mean depth of penetration in the dermis, with a common detector of a person for analysis in a noninvasive analyte property determination system, comprising the steps of: probing skin with a range of illumination zone-to-detection zone distances with at least two wavelength ranges, which optionally overlap, and detecting, using a common detector, illumination zone-to-detection zone distances having mean optical pathways probing the common tissue layer, such as without the mean optical pathways entering the subcutaneous fat layer of the person. Optionally, the skin tissue layers are modulated and/or treated via tissue displacement before and/or during data collection.

17 Claims, 14 Drawing Sheets

Related U.S. Application Data application No. 16/691,615, filed on Nov. 22, 2019, and a continuation-in-part of application No. 15/829,877, filed on Dec. 2, 2017, now abandoned, which is a continuation-in-part of application No. 15/636,073, filed on Jun. 28, 2017, now abandoned.

(60) Provisional application No. 62/355,507, filed on Jun. 28, 2016.

(51) Int. Cl.
*A61B 5/00* (2006.01)
*A61B 5/1455* (2006.01)

(52) U.S. Cl.
CPC .......... *A61B 5/1455* (2013.01); *A61B 5/6832* (2013.01); *G01J 2003/102* (2013.01)

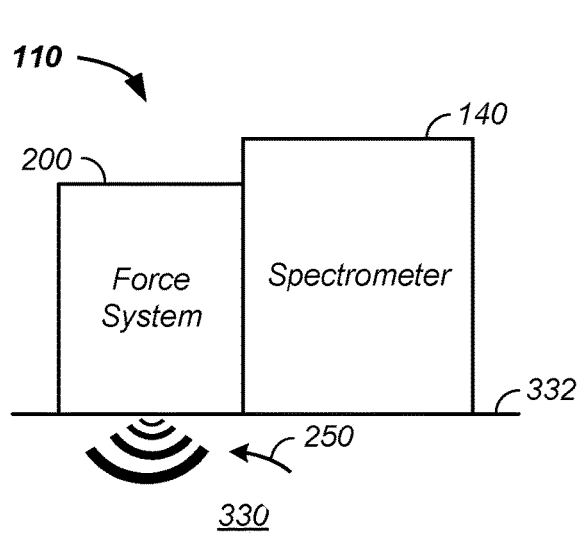
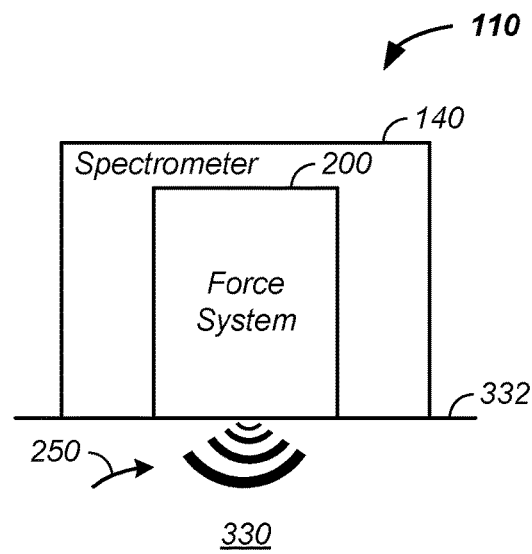
FIG. 5A  FIG. 5B
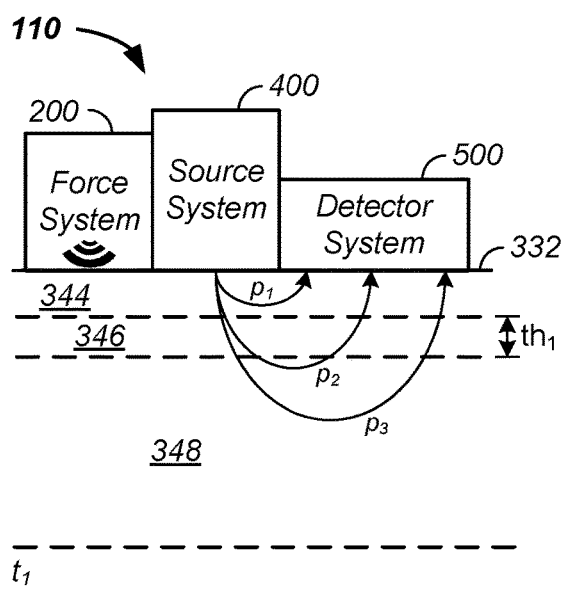
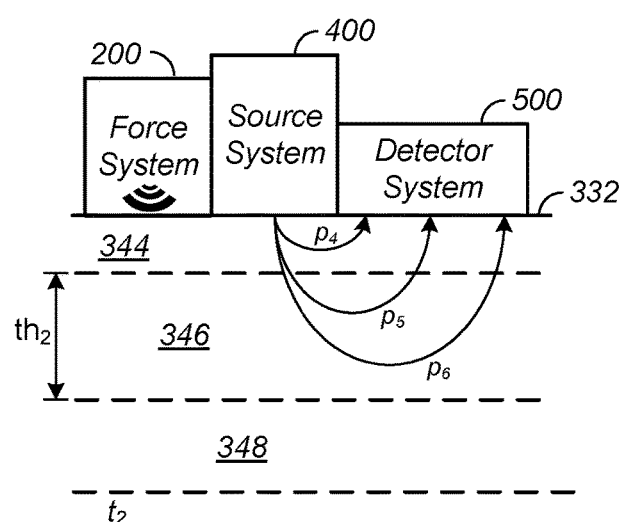
FIG. 6

COMMON DEPTH NONINVASIVE GLUCOSE CONCENTRATION DETERMINATION ANALYZER APPARATUS AND METHOD OF USE THEREOF

CROSS-REFERENCES TO RELATED APPLICATIONS

This application is:

a continuation-in-part of U.S. patent application Ser. No. 16/691,611 filed Nov. 22, 2019;

a continuation-in-part of U.S. patent application Ser. No. 16/691,615 filed Nov. 22, 2019; and a continuation-in-part of U.S. patent application Ser. No. 15/829,877 filed Dec. 2, 2017, which is a continuation-in-part of U.S. patent application Ser. No. 15/636,073 filed Jun. 28, 2017, which claims benefit of U.S. provisional patent application No. 62/355,507 filed Jun. 28, 2016.

BACKGROUND OF THE INVENTION

Field of the Invention

The invention relates generally to noninvasively determining glucose concentration in a living body using an optical analyzer, such as a visible/near-infrared noninvasive glucose concentration determination analyzer.

Discussion of the Prior Art

There exists in the art a need for noninvasively determining glucose concentration in the human body.

SUMMARY OF THE INVENTION

The invention comprises a noninvasive glucose concentration analyzer apparatus and method of use thereof.

DESCRIPTION OF THE FIGURES

A more complete understanding of the present invention is derived by referring to the detailed description and claims when considered in connection with the Figures, wherein like reference numbers refer to similar items throughout the Figures.

FIG. 5A illustrates a force system coupled to a spectrometer and FIG. 5B illustrates a force system embedded in a spectrometer;

FIG. 6 illustrates photons interacting with applied force wave(s) in tissue;

Figure 1:
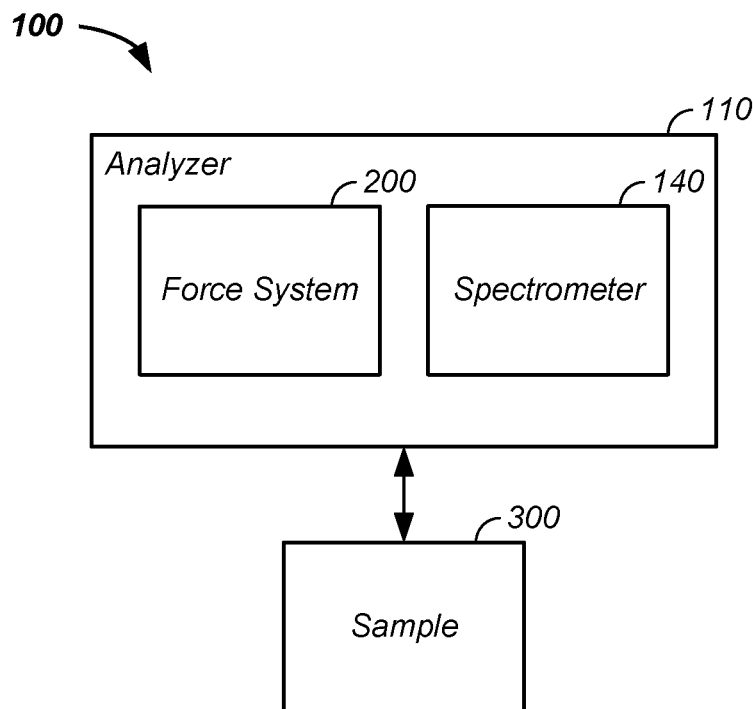
FIG. 1 illustrates use of an applied force-optic analyzer.

Elements and steps in the figures are illustrated for simplicity and clarity and have not necessarily been rendered according to any particular sequence. For example, steps that are performed concurrently or in different order are illustrated in the figures to help improve understanding of embodiments of the present invention.

Problem

There remains in the art a need for a noninvasive glucose concentration analyzer.

DETAILED DESCRIPTION OF THE INVENTION

The invention comprises a method and apparatus for sampling optical pathways having a common tissue depth, such as a maximum mean depth of penetration in the dermis, with a common detector of a person for analysis in a noninvasive analyte property determination system, comprising the steps of: probing skin with a range of illumination zone-to-detection zone distances with at least two wavelength ranges, which optionally overlap, and detecting, using a common detector, illumination zone-to-detection zone distances having mean optical pathways probing the common tissue layer, such as without the mean optical pathways entering the subcutaneous fat layer of the person. Optionally, the skin tissue layers are modulated and/or treated via tissue displacement before and/or during data collection.

Herein, generally, when describing an optical portion of the applied force-optic analyzer, a z-axis is aligned with a mean direction of the photons in a given sub-portion of the analyzer, such as along a longitudinal path of the photons into skin of a subject, and x- and y-axes form a plane perpendicular to the z-axis, such as at an interface point of incident photons into the skin of the subject. At the point of contact of the applied force-optic analyzer with the biological sample, the z-axis is normal/perpendicular to the sample and the x/y-plane tangentially contacts the sample. For instance, the light moves dominantly along the z-axis along vectors approaching perpendicular to an upper arm of a subject or a patient and the x/y-plane tangentially touches the upper arm along the z-axis. In particular cases, a second x,y,z-axis system is used to describe the sample itself, such as a z-axis being along the longitudinal length of a body part, such as along a digit or a finger or along the length of an arm section and the x/y-plane in this case is a cross-section plane of the body part.

A sample is optionally any material responding to an applied physical force in a manner observed by a probing optical system. However, for clarity of presentation and without loss of generality, the sample is described as a person, subject, patient, and/or a living tissue, such as skin and/or a portion of a human or animal. While the analyzer is described as a noninvasive analyzer probing into and optionally through the outer layers of skin, the noninvasive analyzer is optionally used as and or in conjunction with a minimally invasive glucose concentration analyzer and/or in conjunction with an invasive glucose concentration analyzer.

Herein, an illumination zone and/or an imaging zone is a point, region, or area of intersection of the illumination/imaging beam and/or pulse with an incident surface of the sample to yield a spectrum and/or an image of a desired volume of the sample. Herein, a detection zone is a point, region, or area of the sample sampled and/or visualized by one or more detectors. Similarly, herein an applied force zone is an incident point, region, or area of intersection at which an applied force is applied to the sample and a detected force zone is a point, region, or area of the sample interfacing with a force detector.

Applied Force-Optic Analyzer

Referring now to FIG. 1, a noninvasive analysis system 100 using an analyzer 110, such as an applied force-optic analyzer system is illustrated. Generally, an optional force system 200 is used to apply one or more applied forces, physical distortions, and/or force waves to a sample 300. The applied force travels with a wave front, as a wave, in a pattern of compression and rarefication, and/or as a traveling displacement through the sample 300 or portions thereof. With or without application of the force waves, a spectrometer 140 is used to noninvasively collect spectra of the sample 300 and photometrically determine one or more properties of the sample, such as a glucose concentration. As described infra, the applied force is optionally in the form of an acoustic wave. However, the applied force is optionally and preferably a physical displacement of a portion of skin of a person, where the physical displacement is caused by movement of a mechanical object relative to the body to yield a time varying displacement of skin and/or constituents of the skin by the mechanical object. As described, infra, a variety of force provider technologies are available to variably displace the skin in a controlled manner. For clarity of presentation and without loss of generality, a transducer is used as an example to represent an applied force section of the force system 200, where a transducer comprises a device that receives a signal/force in the form of one type of energy and converts it to a signal/force in another form. Again for clarity of presentation and without loss of generality, a piezoelectric actuator is used to represent a transducer and an off-center spinning mass is used to represent a transducer. Hence, again for clarity of presentation and without loss of generality, a piezoelectric-optical analyzer or simply a piezo-optic analyzer, a transducer, and/or a transducer force applicator is used to describe any and all applied force electromechanical sources in the force system 200. Optionally, more than one transducer is used to yield displacement of the surface of the skin/skin, such as at a function of time and/or position.

Figure 2:
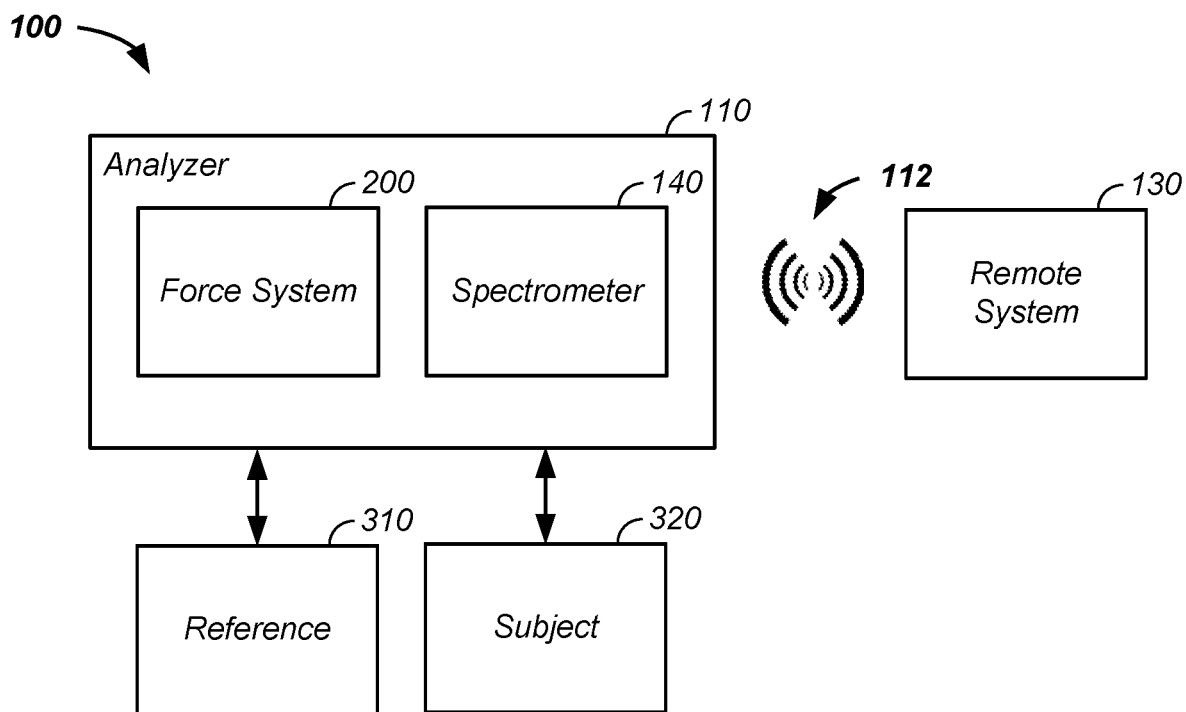
FIG. 2 illustrates a noninvasive analyzer.

Referring now to FIG. 2, use of the analyzer 110 is described. Generally, the analyzer 110 is optionally calibrated using a reference 310 and is used to measure a subject 320, where the subject 320 is an example of the sample 300. Optionally and preferably, the analyzer 110 and/or a constituent thereof communicates with a remote system 130 using a wireless communication protocol 112 and/or a wired communication protocol.

Force System

Referring now to FIGS. 3(A-E), the force system 200 is further described. Generally, the force system 200 comprises a force delivery transducer that directly and/or indirectly contacts the sample 300, such as an outer skin surface 330 of the subject 320 and/or a patient. The subject 320 has many skin layers 340, which are also referred to herein as tissue layers. For clarity of presentation, the skin layers 340 are represented as having a first skin layer, such as a stratum corneum 342; a second skin layer, such as an epidermis 344 or epidermal layer; a third skin layer, such as a dermis 346 or dermis layer; and a fourth layer, such as subcutaneous fat 348 or a subcutaneous fat layer. It is recognized that skin is a complex organ with many additional layers and many sub-layers of the named layers that vary in thickness and shape with time. However, for clarity of presentation and without loss of generality, the stratum corneum, epidermis, dermis, and subcutaneous fat layers are used to illustrate impact of the force delivery transducer on the skin layers 340 of the subject 320 and how the applied force waves alter optical paths of probing photons in the spectrometer 140 of the analyzer 110 in the noninvasive analysis system 100.

Figure 3A:
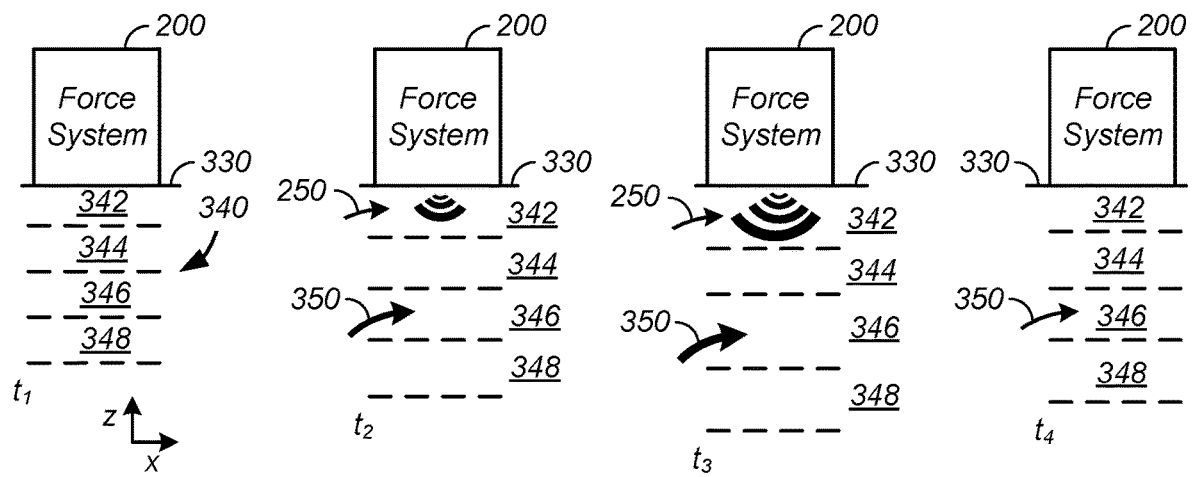
FIG. 3A illustrates an applied force system.
Figure 3B:
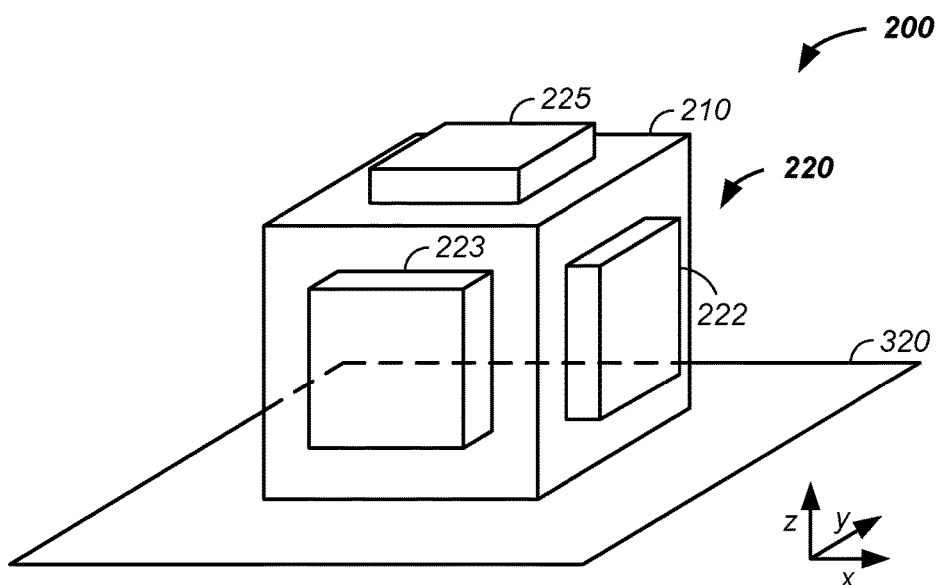
FIG. 3B illustrates a transducer.
Figure 3C:
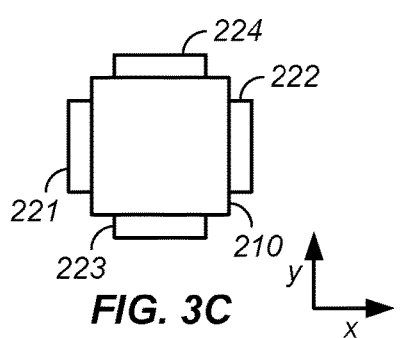
FIG. 3C illustrates transducer movement normal to an optical axis.
Figure 3D:
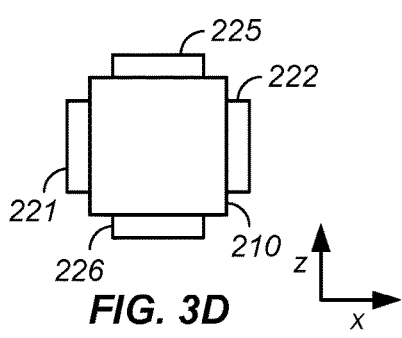
FIG. 3D illustrates a z-axis transducer.
Figure 3E:
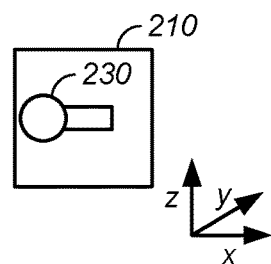
FIG. 3E illustrates a multi-axes off-center spinning mass transducer.

Still referring to FIG. 3A, at a first time, $t_1$, the tissue layers 340 are in a first state. As illustrated, the tissue layers 340 are in a compressed state 340, such as a result of mass of the force system 200 sitting on the skin surface 330, as a result of dehydration of the subject 320, and/or as a result of a physiological and/or environmental force on the tissue layers 340 of the subject. At a second time, $t_2$, the force system 200 applies a force wave 250 to the skin surface 330 of the patient 320, which sequentially propagates into the stratum corneum 342, epidermis 344, dermis 346, and given enough force into the subcutaneous fat 348. In additional to the force wave propagating into the skin layers 340 along the z-axis, the force wave propagates radially through the skin layers, such as along the x/y-plane of the skin layers. As illustrated at the second time, $t_2$, as the force wave 250 propagates into the tissue layers 340, the tissue layers expand and/or rarefy, such that the thickness of the epidermis 344 and/or the dermis 346 layers expands. The rarefication of the epidermis 344 and particularly the dermis 346 allows an increased and/or enhanced perfusion of blood 350 into the rarefied layers. The increased prefusion increases water concentration in the perfused layers, increase and/or changes distance between cells in the perfused layers, and/or changes shapes of cells in the perfused layers, such as through osmolarity induced changes in concentration in and/or around blood cells, such as red blood cells. Generally, scattering coefficients of the epidermis layer and/or especially the dermis layer changes, which is observed by the spectrometer 140 in the range of 400 to 2500 nm with larger changes at smaller wavelengths in the visible, 400 to 700 nm, and/or near-infrared, 700 to 2500 nm, regions. As illustrated at the third time, $t_3$, as the force wave 250 continues propagation in the tissue layers 340, the perfusion 350 continues to increase, such as to a maximum perfusion. As illustrated at the fourth time, $t_4$, after discontinuation of the force wave 250, the skin layers 340 revert toward the initial state of the non-force wave induced perfusion to a local minimum perfusion, which may match the initial perfusion, is likely higher than the initial perfusion, and is at times less than the initial perfusion due to changes in state of the environment, such as temperature, and/or generalized state of the subject 320, such as hydration, localized hydration of skin, such as due to food intake, insulin response to food intake, exercise level, blood pressure, and/or the like. Generally, the tissue layers 340 of the subject increase in thickness and/or rarefy during application of the transducer applied force wave 250 and decrease and/or compress after termination of the transducer applied force wave 250 to the skin surface 330 of the subject 320. The process of applying the force wave 250 is optionally and preferably repeated n times, where n is a positive integer of greater than 1, 2, 5, 10, 100, 1000, or 5000 times in a measurement period of an analyte of the subject 320, such as a glucose concentration. Generally, the cycle of applying the force wave 250 results in a compression-rarefication cycle of the tissue that alters an observed scattering and/or absorbance of probing photons in the visible and near-infrared regions. The force wave 250 is optionally and preferably applied as a single ping force in a tissue state classification step, as multiple pings in a tissue classification step, and/or as a series of waves during a tissue measurement step. Individual waves of a set of force waves are optionally controlled and varied in terms of one or more of: time of application, amplitude, period, frequency, and/or duty cycle.

Still referring to FIG. 3A and referring now to FIGS. 3(B-D), a force wave input element 210 of the force system 200 is illustrated. As illustrated, the force wave input element 210 is equipped with one or more transducers: a left transducer 221, a right transducer 222, a front transducer 223, a back transducer 224, a top transducer 225, and/or a bottom transducer 226. For instance, the left and/or right transducers 221, 222 move the force wave input element 210 left and/or right along the x-axis; the front and/or back transducers 223, 224 move the force wave input element 210 forward and/or back along the y-axis; and/or the top and bottom transducers 225, 226 move the force wave input element 210 up and/or down along the z-axis along and/or into the skin surface 330 of the subject 320, which moves the skin, skin layers 340, and/or skin surface 330 of the subject relative the spectrometer 140 and/or is a source of the force wave 250 moving, in the skin layers 340, along the z-axis into the skin, and/or radially outward from an interface zone of the force wave input element 210 of the force system 200. A transducer itself is optionally used as the force wave impulse element 210. Referring now to FIG. 3E, one or more off-center mass elements 230 is optionally spun or rotated, such as with an electric motor, along one or more of the x,y,z-axes to move the force wave input element 210 relative to the skin surface 330 of the subject 320 resulting movement of the skin of the subject 320 relative to the spectrometer 140 and/or cycling and/or periodic displacement of the tissue layers 340 of the subject 320 due to movement of the force wave input element 210 resulting in the force wave(s) 250. Generally, the force system 200 induces a movement of a sampled zone of skin of the subject 320, applies a displacement of a sampled zone of the skin of the subject 320, and/or applies a propagating force wave into and/or through a sample zone of tissue layers 340 of the subject, where the sampled zone is probed using photons from the spectrometer 140 and/or is measured using a set of detection zone transducers, described infra. The force wave(s) are optionally and preferably applied as a single input ping wave, a set of input ping waves, and/or are applied with a frequency of 0.01 Hz to 60 Hz. Optionally and preferably, the force waves 250 are applied with a frequency greater than 0.01, 0.02, 0.05, 0.1, or 1 Hz. Optionally and preferably, the force waves 250 are applied with a frequency of less than 200, 100, 50, 40, 30, or 20 Hz. Optionally and preferably, the force waves 250 are applied with a frequency within 5, 10, 25, 50, or 100 percent of 2, 4, 6, 8, 10, 12, 15, and 20 Hz.

Optical System

Figure 4A:
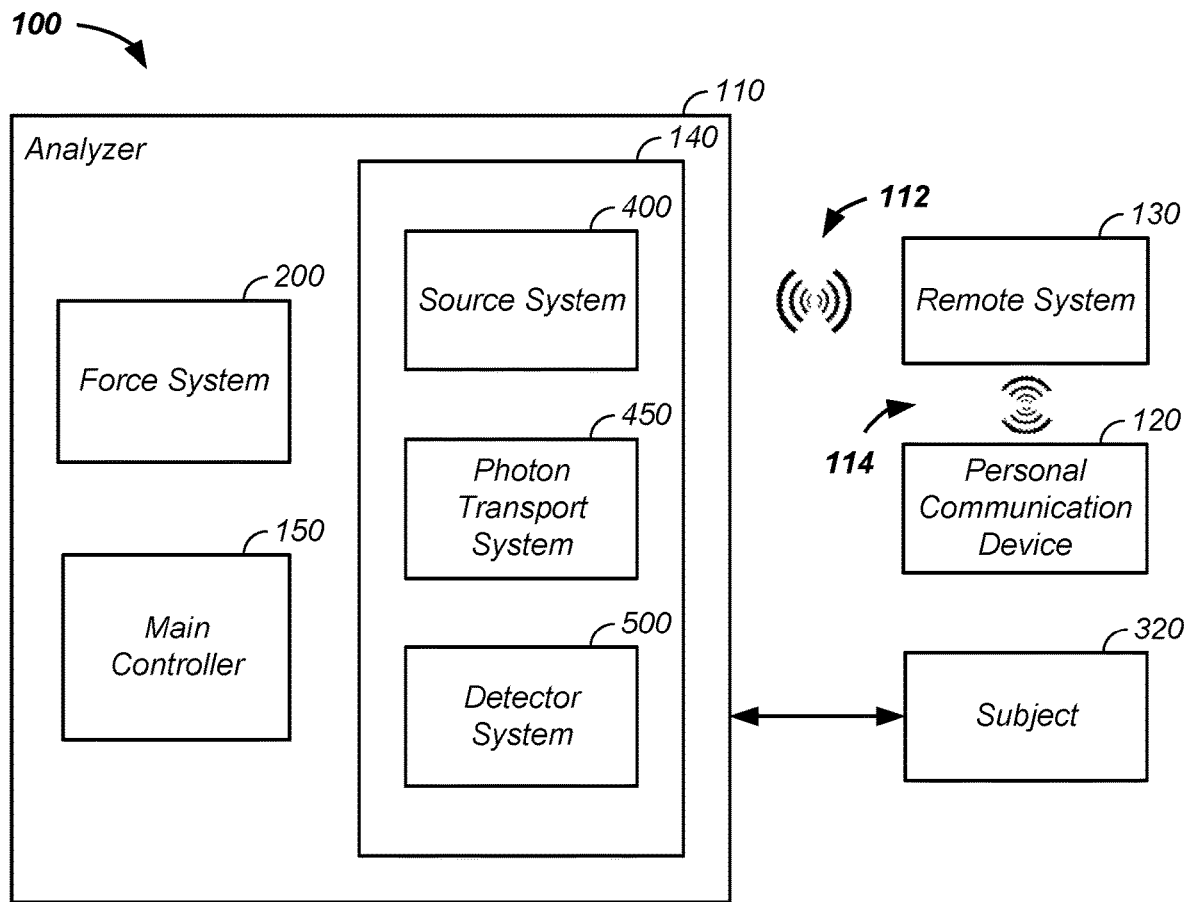
FIG. 4A illustrates spectrometer components.

Referring now to FIG. 4A, the spectrometer 140 of the analyzer 110 is further described. The spectrometer 140 comprises a source system 400, which provides photons 452 in the visible and/or infrared regions to the subject 320, such as via a photon transport system 450, at an illumination zone. After scattering and/or absorbance by the tissue layers 340 of the subject 320, a portion of the photons are detected at a detection zone by a detector system 500. The source system 400 includes one or more light sources, such as any of one or more of a light emitting diode, a laser diode, a black body emitter, and/or a white light source, that emits at any wavelength, range of wavelengths, and/or sets of wavelengths from 400 to 2500 nm. Each source system photon source is optionally controlled in terms of time of illumination, intensity, amplitude, wavelength range, and/or bandwidth. The photon transport system 450 comprises any fiber optic, light pipe, air interface, air transport path, optic, and/or mirror to guide the photons from the light source to one or more illumination zones of the skin surface 330 of the subject 320 and/or to guide the photons from one or more detection zones of the skin surface 330 of the subject 320 to one or more detectors of the detector system 500. Optionally and preferably, the photon transport system 450 includes one or more optical filters and/or substrates to selectively pass one or more wavelength regions for each source element of the source system 400 and/or to selectively pass one or more wavelength ranges to each detector element of the detector system 500. Herein, the reference 310 is optionally an intensity and/or wavelength reference material used in place of the sample and/or is used in a optical path simultaneously measured by the analyzer 110.

Figures 4B, 4C:
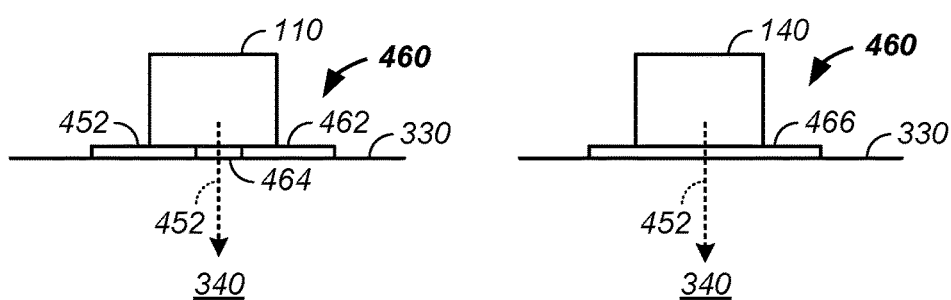
FIG. 4B illustrates an affixing layer.
FIG. 4C illustrates a coupling fluid enhanced affixer.

Still referring to FIG. 4A and referring now to FIG. 4B and FIG. 4C, the subject 320 optionally and preferably wears the analyzer 110 in the physical form of a watch head, band, and/or physical element attached to the body with a band and/or an adhesive. For example, the analyzer 110, the spectrometer 140, the source system 400, and/or the photon transport system 450 is optionally attached to the subject 320, such as at the wrist or upper arm, using thin affixing layer 460, such as a double sided adhesive 462. Referring now to FIG. 4B, the double sided adhesive 462 optionally contains an aperture 464 therethrough. The photons 452 optionally and preferably pass through the aperture 452 to the skin surface 330 of the subject. The force wave 250 optionally moves the skin surface 330 through the aperture into intermittent contact with the analyzer 110. Optionally, referring now to FIG. 4C, a thin affixing layer 466, such as less than 1, 0.5, or 0.25 mm thick, is continuous in nature in front of the incident surface and/or incident photon coupling zone and/or is continuous in nature in front of the detection zone, where photons exiting the skin surface 330 are detected by the detector system 500. The affixing layer 466 is optionally permeated with a fluid, such as a coupling fluid, an air displacement medium, an optical coupling fluid, a fluorocarbon liquid, a fluorocarbon gel, an index of refraction matching medium, and/or any fluid that increases a percentage of photons from the source system 400 entering the skin surface 330 compared to an absence of the fluid and/or is any fluid that increases a percentage of photons from the tissue layers 340 exiting the detection zone and reaching the detector system 500 as compared to a case where the fluid is not embedded into the affixing layer. Hence, the affixing layer serves several purposes: attaching the analyzer or a portion thereof to the skin surface 330 of the subject 320, coupling forces from the force system 200 to the skin surface 330 of the subject 320, forming a constant sampling interface location on the skin surface 330 of the subject, and/or altering a coupling efficiency, angular direction, and/or reproducibility of coupling of photons enter the skin of the subject 320 and/or exiting the skin surface 330.

Coupled Force System/Spectrometer

Referring now to FIG. 5A and FIG. 5B, the force system 200 is illustrated working in conjunction with the spectrometer 140. Referring now to FIG. 5A, the analyzer 110 is illustrated with the force system 200 being attached to and/or within 1, 2, 3, 5, 10, 20, or 50 mm of the spectrometer 140. Referring now to FIG. 5B, the analyzer 110 is illustrated with the force system 200 being integrated into the spectrometer 140, such as within 20, 10, 5, 2, or 1 mm of the source system 400 of the analyzer 110 and/or in a single housing unit of the analyzer 110.

Several examples are provided that illustrate how the force system 200 alters the tissue layers 340 of the subject 320 and how a selection of detected signals from the spectrometer 140 is performed as a function of time and respective radial separation between the one or more illumination zones and the one or more detection zones, such as using water signal, fat signal, and/or protein signal to determine the correct detection signals to use for noninvasive glucose concentration determination.

EXAMPLE I

Referring now to FIG. 6, a first example of the analyzer 110 using the force system 200 and the source system 400 at the same time and/or within less than 60, 30, 15, 10, 5, or 1 second of each other is provided. In this example, the force system 200 applies a force to the tissue layers 340 at a first time, $t_1$, when the dermis has a first mean z-axis thickness, $th_1$. Optionally and preferably, the analyzer 110 acquires signals representative of the tissue layers 340 of the subject 320 using the source system 400 and the detector system 500. Illustrated are three representative photon pathways, $p_{1-3}$, reaching the detector system 500, such as at a first detector element, a second detector element, and a third detector element, respectively, at the first time, $t_1$, and/or within less than 60, 30, 15, 10, 5, or 2 seconds from the first time, $t_1$. Notably, at the first time, the first photon pathway, $p_1$, has an average path that does not penetrate into the dermis 346, while the second and third photon pathways, $p_{2-3}$, have mean pathways that penetrate through the dermis into the subcutaneous fat 348. In at least one preferred use of the analyzer, noninvasive glucose concentration determination is performed using a mean photon pathway that penetrates into the dermis 346 and not into the subcutaneous fat 348 and/or uses signal from a detector element at a first/minimal radial distance from the illumination zone, where the first/minimal radial distance is the smallest radial distance observing an increase in a fat signal/dominantly fat related signal, such as from the subcutaneous fat 348, compared to a water signal/dominantly water related signal from skin layers 340 closer to the skin surface 332 than that subcutaneous fat 348. Examples of wavelengths containing dominantly water absorbing signals are wavelengths correlating with the peaks of the water absorbance bands 710, FIG. 7A, and/or peaks of the protein absorbance bands, FIG. 7B, and examples of wavelengths containing an increased fat absorbance to water absorbance ratio when a mean photon path enters the subcutaneous fat 348 are at the fat absorbance bands 720. For instance, a protein band-to-fat band ratio optionally compares the protein absorbance band at 1690 nm with the fat absorbance band at 1715 nm, where either range is ±5 or 10 nm. Still referring to FIG. 6, at a second time, $t_2$, the force wave 250 from the force system 200 has expanded the dermis layer to a second thickness, $th_2$, which is at least 0.1, 0.2, 0.3, 0.5, 1, 2, 5, 10, 20, or 50% thicker than the first thickness, $th_1$, and/or has an increased water absorbance, as measure by the first, second, and/or third detector element of the detector system 500, representative of the first through third photon pathway, $p_{1-3}$, in the condition of the larger dermis thickness at the second time, $t_2$, as represented by a fourth, fifth, and sixth photon pathway, $p_{4-6}$. Notably, the fifth and sixth photon pathways, $p_{5,6}$, with the same illumination zone to detection zone radial distance as the first and second photon pathways, $p_{1-2}$, have mean photon pathways that penetrate into the dermis 346 and not into the subcutaneous fat 348. Thus, the water-to-fat ratio and/or the protein-to-fat absorbance ratio of the observed signal continues to increase with radial distance for the second and third detectors after the force system 200 increased the thickness of the dermis 346 to the second thickness, $th_2$. Again, at least one preferred measurement/metric is a measurement with a higher water-to-fat absorbance ratio and/or a higher protein-to-fat absorbance ratio as the metric indicates that the photons are sampling the dermis 346 without undue sampling of the subcutaneous fat 348. In this example, at the second time, the water-to-fat absorbance ratio of the fifth optical path, $p_5$, is greater than observed with the second optical path, $p_2$, despite have the same source zone-to-detector zone radial distance. Further, in this example a preferred optical signal is from the sixth optical path, $th_6$, at the second time, $t_2$, with a largest ratio of mean pathlength in the dermis 346 to total mean detected pathlength. For illumination zone-to-detector zone distances established to sample the dermis 346, as discussed infra, determining a current thickness of the protein/water rich dermis 346 yields knowledge of an appropriate glucose illumination zone-to-glucose detection zone, such as for photons in the range of 1500 to 1600 nm. FIG. 7C illustrates increased scattering with decreasing wavelength at a first scattering coefficient, $\mu_{s1}$, 740 and a second scattering coefficient, $\mu_{s2}$, 750.

EXAMPLE II

Figure 8:
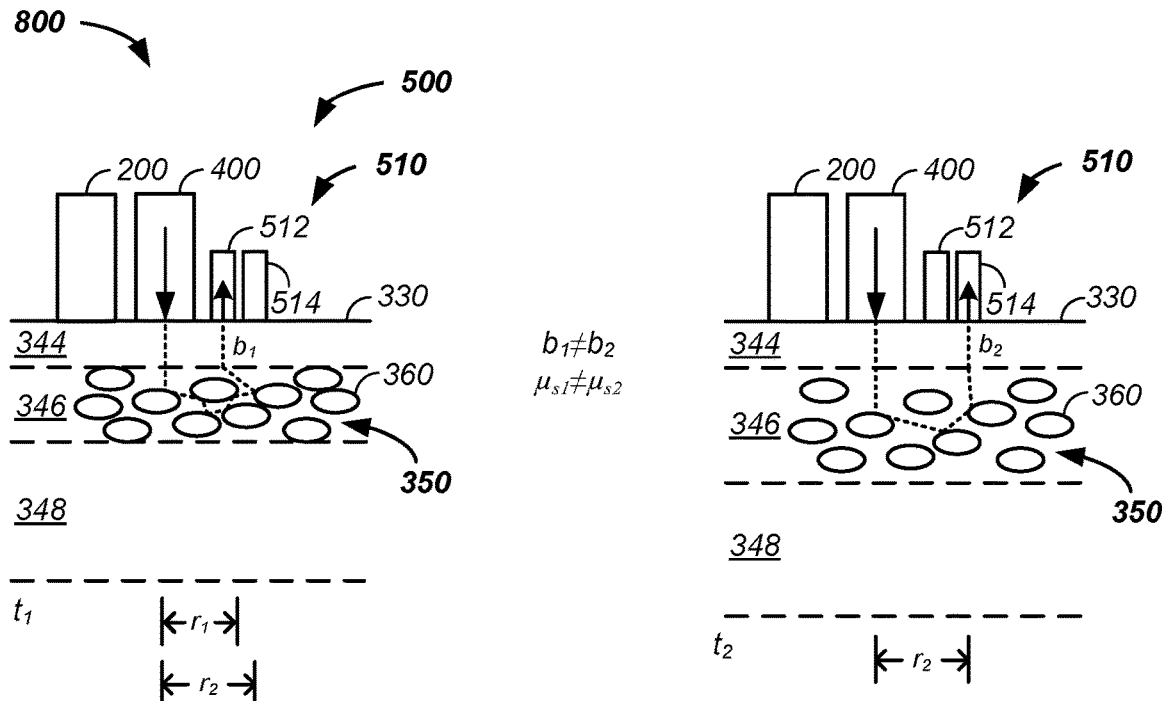
FIG. 8 illustrates detector selection.

Referring now to FIG. 8, a second example is provided where the analyzer 110 uses the force system 200 to alter the sample 300 to enhance a noninvasive analyte property determination using the spectrometer 140. As above, the force system 200 provides one or more force waves 250 into the subject 320, which alters positions of cells 260 in the dermis 346 relative to the illumination zone of the illumination system 400 and or relative to one or more detection zones associated with a single element detector and/or one or more detectors of an array of detector elements 510. As illustrated, the cells 360 have a first average intercellular distance at a first time, $t_1$, which is altered by application of the force wave 250 to a second average intercellular distance at a second time, $t_2$, where the net change in cell position alters detected spectrophotometric absorbance signals at a give detector element of the detector system 500 by greater than 0.01, 0.02, 0.05, 0.1, 0.5, 1, 2, 5, or 10 percent, such as by a change in observed scattering and/or observed absorbance at a fixed radial distance between an illumination zone and a detection zone. Similarly, the average percentage volume of the intercellular fluid 350 in the dermis layer differs by greater than 0.01, 0.02, 0.05, 0.1, 0.5, 1, 2, 5, or 10 percent as a result of the applied force wave(s) 250. All of a change in thickness, change in observed mean pathlength, change in radial distance of detection, change in mean intercellular spacing, change in scattering, and change in water concentration, related to perfusion, are illustrated between the first time, $t_1$, and the second time, $t_2$, as a result of the applied force wave 250. Notably, a selected detector signal from the array of detectors 510 changed from a second detector element 512 at a first radial distance, $r_1$, from the illumination zone to a fourth detector element 514 at a second radial distance, $r_2$, from the illumination zone based on the above described larger observed water signal-to-observed fat signal ratio and/or as the second pathlength, $b_2$, is longer than the first pathlength, $b_1$, in the dermis layer. Similarly, absorbances of skin constituents, such as protein, albumin, globulin, keratin, and/or elastin increase relative to fat absorbance for the second pathlength, $b_2$, as the mean pathlength spends more time in the dermis layer compared to the subcutaneous fat layer 348, as described supra.

EXAMPLE III

Figure 9:
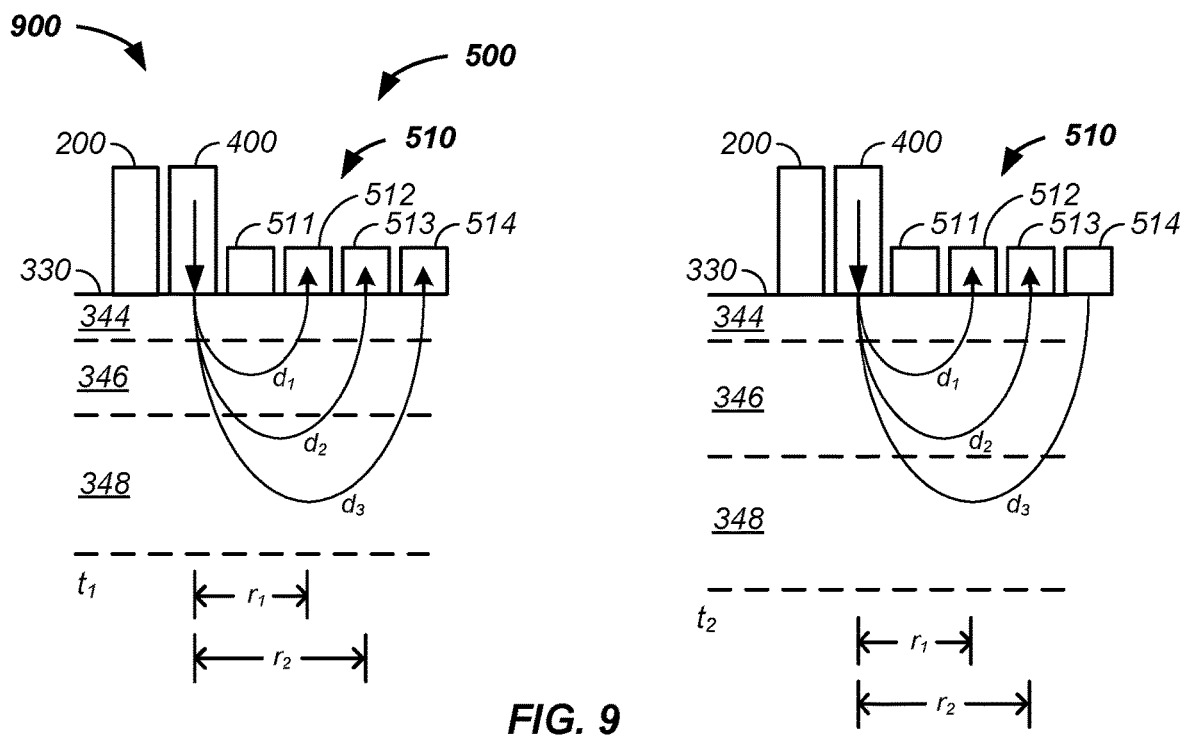
FIG. 9 illustrates changing detector selection with tissue change.

Referring now to FIG. 9, a third example of using the force system 200 to alter properties of the subject 330 to enhance performance of a noninvasive glucose concentration determination using the spectrometer 140 is provided. In this example, the detector array 510 of the detector system 500 contains n detector elements at differing radial distances from a time correlated illumination zone. For clarity of presentation, the detector array 510 is illustrated with four detector elements: a first detector element 511, a second detector element 512, a third detector element 513, and a fourth detector element 514. At a first time, $t_1$, the large water absorbance, protein absorbance, and/or protein and water absorbance-to-fat ratio is observed using the second detector element 512 having a first illumination zone-to-detection zone radial distance, $r_1$, and a first mean optical pathway, $d_1$, penetrating into the dermis 346 with minimal to no mean penetration into the subcutaneous fat 348. However, at a second time, $t_2$, after the provided force wave 250 has altered the skin of the subject 320, the third detector element is observed, at a selected detection point in time, to have the largest metric for detector selection, such as a smoothly falling observed intensity with radial distance at a fat absorbance wavelength, where a sudden decrease in observed intensity at the fat absorbance wavelength indicates mean penetration of the observed optical pathway into the subcutaneous fat 348, such as at the second radial distance, $r_2$. Notably, the largest radial distance is selected for a given water, protein, and/or fat based metric as at the larger radial distance a difference between a shortest possible pathlength between the illumination zone and the detection zone, the radial distance, is closest to the largest possible observed pathlength, which is based upon a maximum observable absorbance by a detector type for a fixed number of photons. For example, if the maximum observable absorbance is 3.9 and the absorbance per millimeter is 1.3, then a maximum observable pathlength is 3.0 mm. If the observed radial pathlength is 1.5 mm then a first range of observed pathlengths is 1.5 to 3.0 mm with a difference of 1.5 mm. Hence, a first ratio of observed pathlength difference to radial distance is 1:1 (1.5 mm:1.5 mm), which is a 100% error. However, if the observed radial pathlength is 2.5 mm, then a second range of observed pathlengths is 2.5 to 3.0 mm with a difference of 0.5 mm. Hence, a second ratio of observed pathlength difference-to-radial distance is 1:5 (0.5 mm:2.5 mm), which is a second pathlength error of 20% or one-fifth of the pathlength error of the first case. In general, the largest radial distance yielding and intensity-to-noise ratio beyond a threshold, such as 0.5, 1, 1.5 or 2, is preferred as error in a range of observed pathlengths decreases, which reduces the error in b, in Beer's Law: equation 1, $$A = \text{molar absorptivity} * b * C \qquad \text{(eq. 1)}$$

where b is pathlength and C is concentration, which is central to visible and near-infrared absorbance and/or scattering models used to determine an analyte property, such as a noninvasive glucose concentration as measured using photons optically probing skin.

Skin State Classification

Skin state is optionally classified using a single force pulse or single impulse function, also referred to herein as a ping. Generally, an applied force, such as the force wave 250 provided by the force system 200, takes time to propagate through the subject 320. The travel time of the force wave varies as a function of state of the body, such as hydration, temperature, glucose concentration, triglyceride concentration, hematocrit and/or any constituent of skin, blood, and/or interstitial fluid. Hence, the amount of time to travel radial distances to force wave detectors is optionally used to classify the state of the subject and/or to map the state of the subject in regions probed by the force wave. For clarity of presentation and without loss of generality, two example of force wave detection are provided here using: (1) a transducer force detector and/or (2) an optical force wave classifier.

EXAMPLE I

Figure 10A:
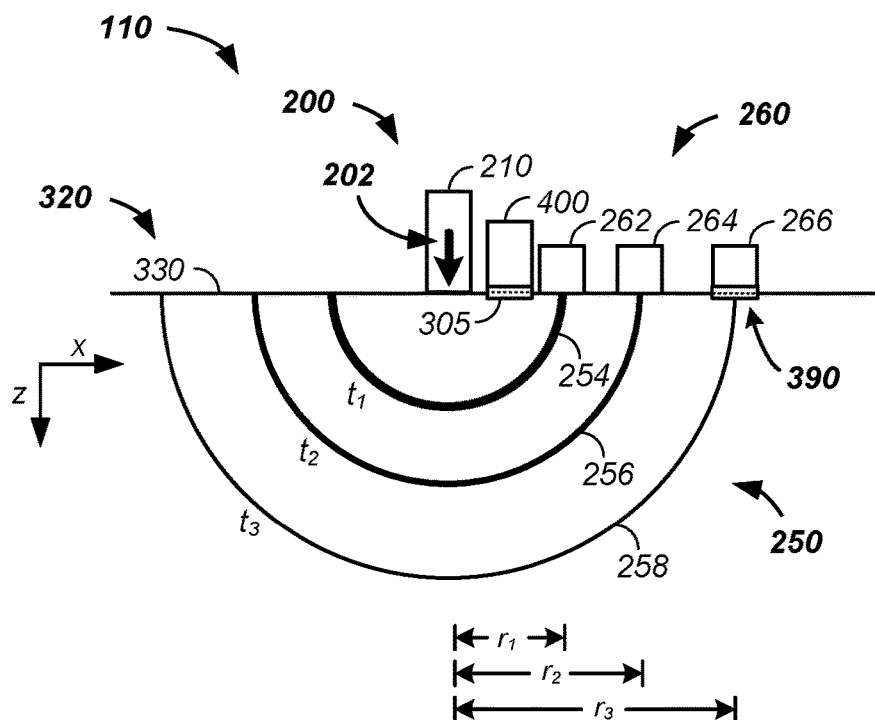
FIG. 10A illustrates a transducer force applicator and FIG. 10B and FIG. 10C illustrate transducer force detectors in lines and arcs respectively.
Figure 10B:
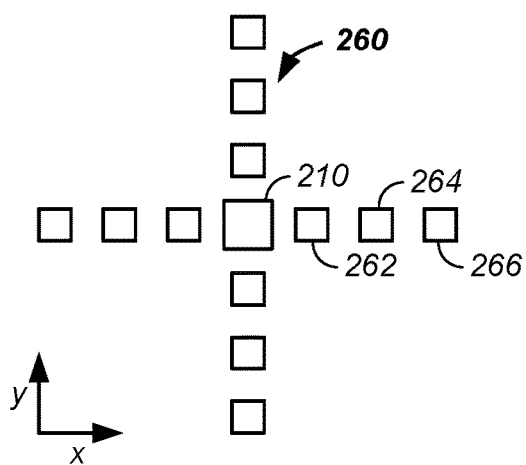
Figure 10C:
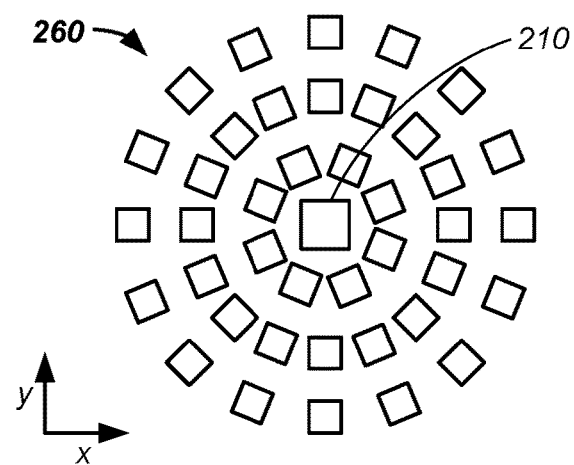

Referring now to FIGS. 10(A-C), transducer force detectors are optionally used to detect transit times of the force wave 250 from the force wave input element 210 to one or more detectors of a set of transducer force detectors 260. Generally, a transducer force detector converts mechanical motion, such as passage of the force wave 250 and/or skin movement into a measured electrical signal. Referring now to FIG. 10A, for clarity of presentation and without loss of generality, a first transducer force detector 262, a second transducer force detector 264, and a third transducer force detector 266 are illustrated that represent n transducer based force detectors, where n is a positive integer of greater than 1, 2, 3, 5, 10, or 20. As illustrated in FIGS. 10B and 10C, the n transducer based force detectors are optionally positioned in a linear array, in a two-dimensional array, and/or along arcs, such as at differing radial distances from one or more light sources in the source system 400. Referring still to FIG. 10A, as illustrated, at a first time, $t_1$, the force wave 250 has propagated to the first transducer force detector 262 as a first wave front position 254; at a second time, $t_2$, the force wave 250 has propagated to the second transducer force detector 264 as a second wave front position 256; and at a third time, $t_3$, the force wave 250 has propagated to the third transducer force detector 266 as a third wave front position 258. Timing of each wave front to each transducer based force wave detector allows: (1) generation of a sub-surface tissue map of constituents of the skin of the subject 320 using mathematical techniques used for seismic mapping known to those skilled in the art of seismic mapping and/or (2) a classification of state of the subject 320 versus a calibration set of classifying states of force wave propagation radial translation times. For instance, the classification is as simple as slow, medium, or fast translation times to a given transducer detector or a more involved combination of translation times for one or more of: (1) responses at a single detector position and (2) responses at a set of detector positions and/or responses to varying inputs of the force wave, such as time, direction, amplitude, and/or frequency of one or more pings from the force wave input elements and/or time varying induced applied pressure and/or displacement of a portion of the skin of the subject 320 by the force system 200.

EXAMPLE II

Figure 11A:
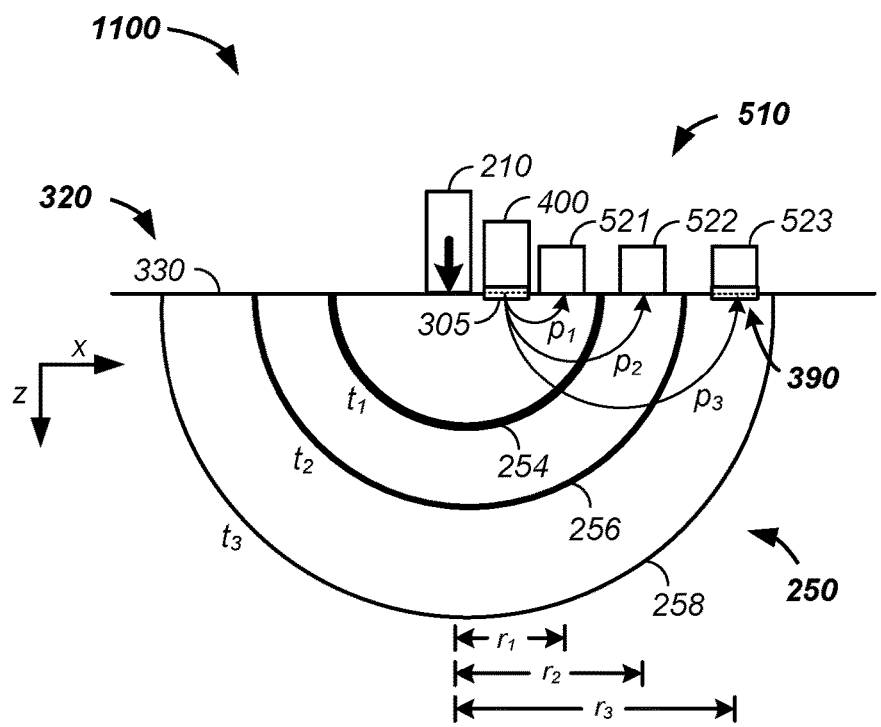
FIG. 11A illustrates radial optical detection of force waves.
Figure 11B:
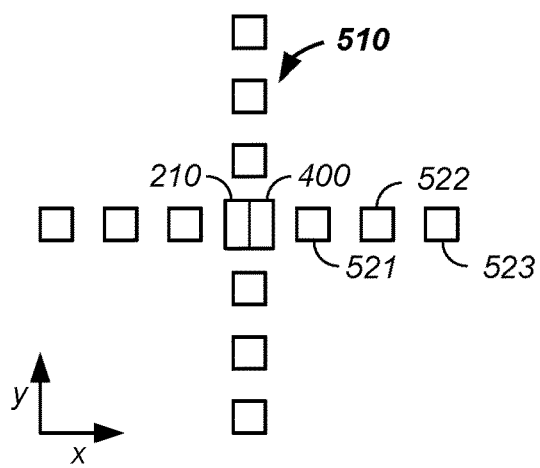
FIG. 11B illustrates an array of optical detectors.
Figure 11C:
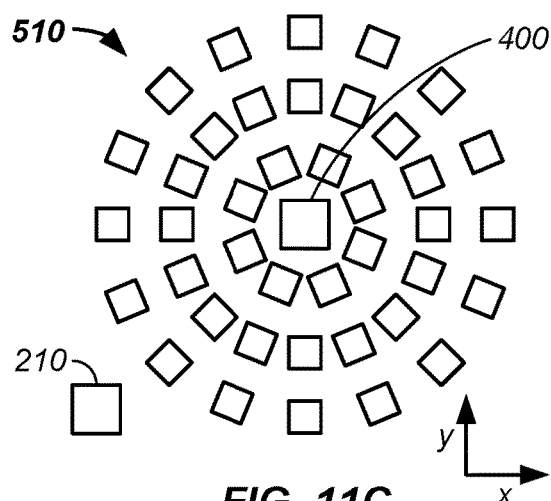
FIG. 11C illustrates arcs of optical detectors.

Referring now to FIGS. 11(A-C), propagation of the force wave(s) 250, such as force wave fronts 254, 256, 258 is detected using a set of optical detectors and using the results in a manner similar to detecting the force wave 250 using the set of transducer based wave detectors. For instance, as the force wave 250 propagates through the tissue layers 340, the density, absorbance, and/or scattering of voxels of the skin of the subject 320 change, which alters an observed mean optical path between a given source of photons and a photon/photonic detector. One or more sources of the source system 400 coupled to the array of optical detector elements 510 via the subject 320 is optionally used to detect propagation times of the force wave(s) 250. For clarity of presentation and without loss of generality, a first optical detector 521, a second optical detector 522, and a third optical detector 523 are illustrated that represent n optical detectors, where n is a positive integer greater than 0, 1, 2, 3, 5, 10, 15, 16, 20, 25, 100, 500, 1000, and 5000. As illustrated in FIGS. 11B and 11C, the n optical detectors are optionally positioned in a linear array, in a two-dimensional array, and/or along arcs, such as differing radial distances from one or more light sources in the source system 400 and/or from one or more force wave sources. Notably, one or more detectors of the array of optical detector elements 510 are optionally and preferably used to detect photons from the source system 400 during a measurement phase of an analyte and/or tissue property with or without a tissue classification step. As illustrated, the first optical detector 521 detects a first optical signal, modified by the force wave 250, with a first pathlength, $p_1$, at a given point in time; the second optical detector 522 detects a second optical signal, modified by the force wave 250, with a second pathlength, $p_2$, at the given point in time; and the third optical detector 523 detects a third optical signal, modified by the force wave 250, with a third pathlength, $p_3$, at the given point in time. Each detected optical signal contains absorbances due to any sample constituent, such as water, protein, fat, and/or glucose and/or is representative of state of the tissue, such as a measure of scattering and/or temperature. As the force wave(s) propagate through the tissue, the first, second, and third pathlengths, $p_1$, $p_2$, $p_3$, vary. Hence, the state of the subject 320 is optionally characterized and/or mapped in a manner similar to the transducer wave detection classification and/or mapping; however, optical signals with chemical meaning are used in the process, such as detected intensity, absorbance, and/or scattering related to temperature, one or more tissue layer properties, collagen, elastin, water, albumin, globulin, protein, fat, hematocrit, and/or glucose, such as a concentration, change in tissue state, or a physical structure.

Referring again to FIG. 11A and FIG. 12A, the applied pressure/force wave/displacement optionally generates a gap and/or varies an applied pressure at a first interface 305 of the source system 400 and the skin surface 330 and/or at a second interface 390 of the detector system 500 and/or any element thereof and the skin surface 330. A resulting air gap between the analyzer 110 and the subject 320 and/or a time varying change between an air gap and contact between the analyzer 110 and the subject 320 is used to determine times of contact/relative contact, which is in turn optionally and preferably used in a selection of detected signals step, described infra. For example, loss of optical contact yields a sudden increase in observed intensity in a wavelength region of high absorbance, such at as region dominated by water absorbance in the range of 1350 to 1550 nm, 1400 to 1500 nm, and/or within 5, 10, 15, 25, and/or 50 nm of 1450 nm. Removal of non-contacting signals aids in the development of an outlier analysis algorithm and/or in determining state of the tissue and/or in determination of a degree of applied force from the source system 400, detector system 500, and/or analyzer 110 to the skin surface 330 of the subject 320 as a function of time and/or position.

Force Wave/Optical Probe Analyte State Determination

Figure 12:
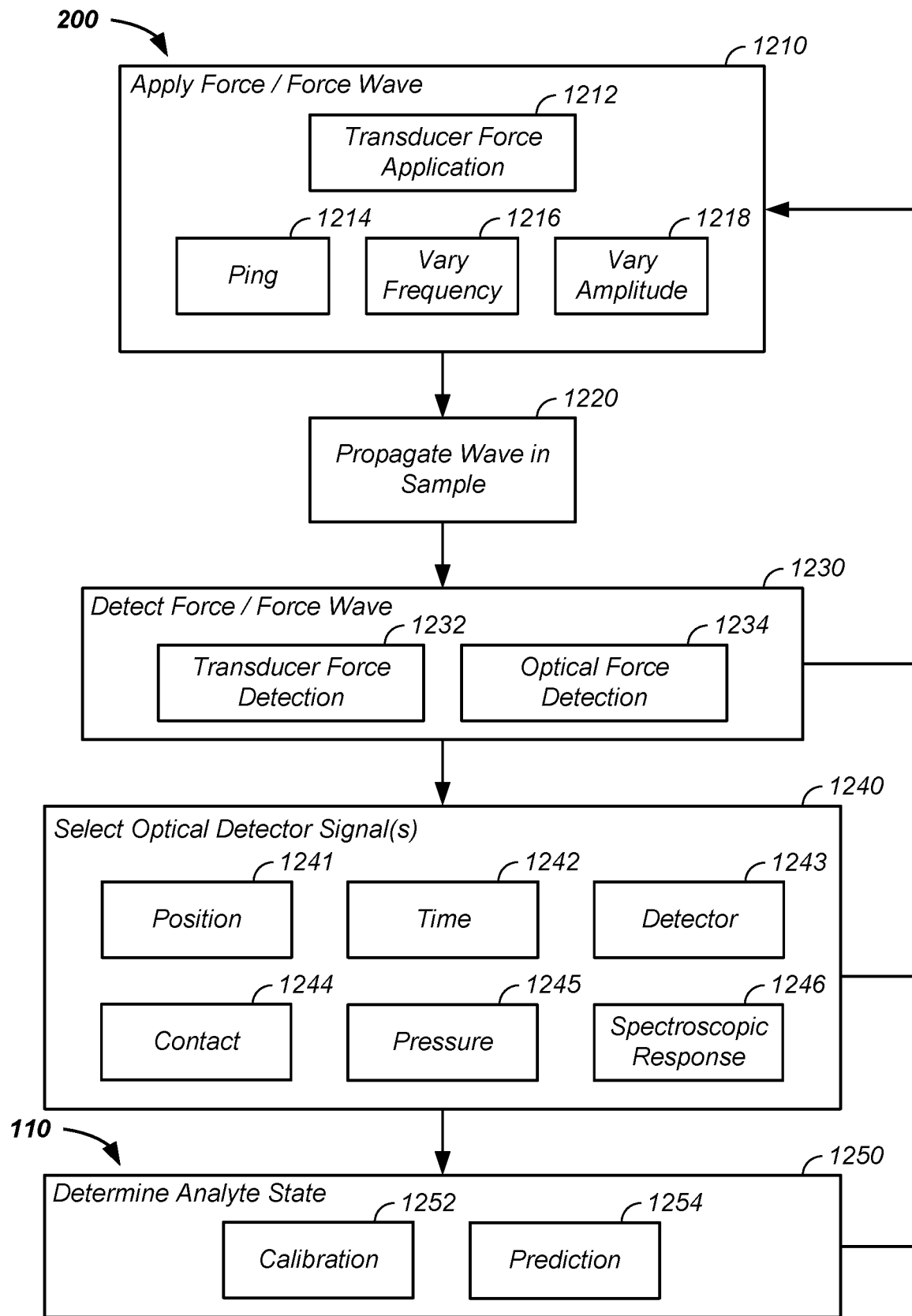
FIG. 12 illustrates optical probes observing tissue modified by force waves in a noninvasive glucose concentration determination system/analyzer.

Referring now to FIG. 12, a process of determining an analyte property, such as a glucose concentration, using one or more optical signals optionally and preferably modified by an applied force, force wave, and/or displacement is provided.

Referring still to FIG. 12, in a process, such as a first process or a second process, a force is applied 1210, such as in the form of a force wave and/or displacement induced force wave. For example, the force wave/displacement is generated with a transducer to generate application of a transducer force 1212, which is a single ping 1214/displacement and/or a series of pings and/or is a force/displacement varied in frequency 1216 and/or varied in amplitude 1218, such as via a controller, such as a main controller of the analyzer 110. Subsequently, the force wave 250/tissue displacement induced pressure propagates in the sample 1220.

Referring still to FIG. 12, in another process, such as a first or second process, a result of the tissue displacement induced force wave is measured and/or detected 1230, such as through a transducer force detection 1232 and/or an optical force detection 1234.

Referring still to FIG. 12, in still another process, such as a second and/or third process, selection of a sub-set of detected signals 1240 is performed, such as a function of position 1241, time 1242, detector 1243, contact 1244, pressure 1245, and/or spectroscopic response 1246 and an analyte state is determined 1250, such as via generation of a calibration 1252 and/or use of a generated calibration in a prediction step 1254.

Multiple-Sensor System

Figure 13:
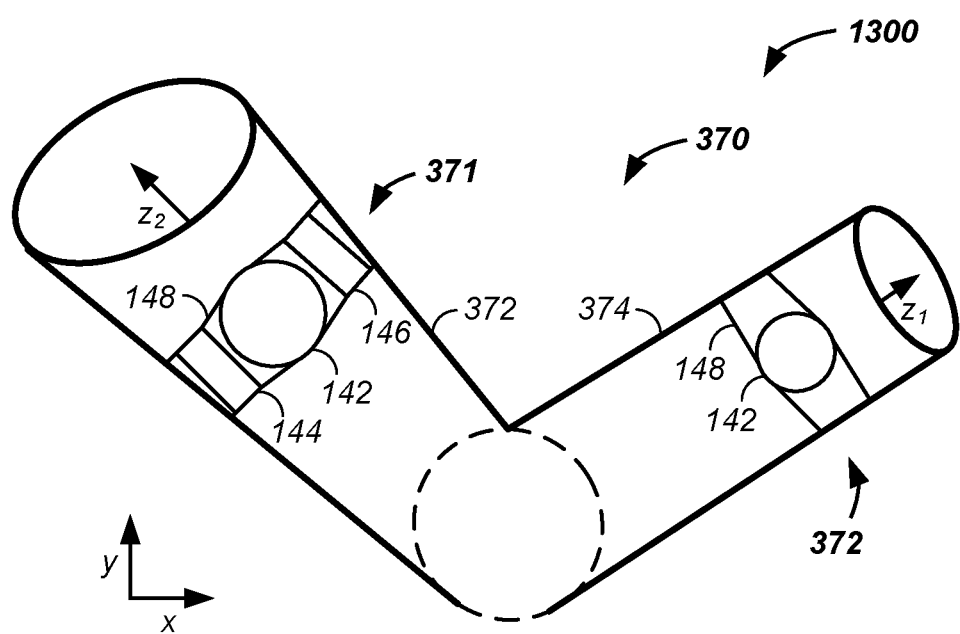
FIG. 13 illustrates a multi-sensor analyzer system.

Referring again to FIG. 4A and referring now to FIG. 13, the analyzer 110 optionally comprises multiple sub-sensor systems that operate independently to collect data but operate in concert for determination of state of the subject 320. For instance the spectrometer 140 optionally comprises a first spectrometer version/system 142 connected/affixed to a first part of the subject 320, such as on the arm of the subject 320, and a second spectrometer system/version 144 connected/affixed to a second part of the subject 320, such as on the leg of the subject 320. Optionally, the spectrometer 140 is affixed to any part of the body, such as an ear lobe, webbing of the hand, forehead, torso, limb, arm, or leg.

Still referring to FIG. 13, generally, the spectrometer 140 refers to n spectrometers/analyzers, where each of the n spectrometers optionally and preferably collects data independently, where n is a positive integer, such as 1, 2, 3, 4, 5, or more. Optionally, each of the n spectrometers collect and analyze data independently. However, preferably, each of the n spectrometers collect data and after little or no pre-processing, collected data is sent to the analyzer 110, a central processor, a personal communication device, such as a cell phone 122, and/or to the web for further processing, which allows a central system to process data from the multiple sub-spectrometer systems.

Still referring to FIG. 13, optionally, each of the n spectrometers are of the same type and design. However, preferably, each of the n spectrometers are distinct in type and/or design. For instance, the first spectrometer version 142 comprises first sources, optics, and detectors that are directed to measurement of a first constituent/property of the subject 320 and the second spectrometer version 144 comprises second sources, optics, and detectors that are directed to measurement of a second constituent/property of the subject 320.

Still referring to FIG. 13, for example, the n spectrometer systems are optionally and preferably configured to interface to separate portions of the body and/or to measure separate and/or overlapping properties/constituents of the subject 320, such as percent oxygen saturation, heart rate, heart rate variability, glucose concentration, protein concentration, fat, muscle, protein concentration, albumin concentration, globulin concentration, respiration rate, an electrocardiogram, blood pressure, and/or body temperature and/or environmental temperature and/or acceleration of the subject 320, such as to indicate a fall of the subject 320 and/or an interfering movement of the subject 320 that affects the measurements of the one or more spectrometers 140.

Still referring to FIG. 13, herein, for clarity of presentation and without loss of generality, the spectrometer 140 is illustrated as a noninvasive glucose concentration analyzer. However, the spectrometer 140 optionally measures any constituent of the body noninvasively, in a minimally invasive manner, and/or operates in conjunction with a noninvasive, minimally invasive, and/or invasive reference system, such as for calibration and quality control procedures. Examples of a first spectrometer version 142 and a second spectrometer version 144 determining an analyte property is provided, infra.

EXAMPLE I

Referring still to FIG. 13, an example of interfacing 1300 the analyzer 110 to an arm 370 of the subject 320 is illustrated. As illustrated, a first analyzer/spectrometer version 371 of the analyzer 110 is coupled to a section of an upper arm 372 of the subject's arm and a second analyzer/spectrometer version 373 of the analyzer 110 is coupled to a forearm/wrist 374 of the patient's arm 320. Notably, the first analyzer version 371 interfaces to the subject 320 at a first interface zone along a first z-axis perpendicular to a first x/y-axis plane that is tangential to the subject 320 and that is independent and different from a second interface of the second analyzer version 373, which interfaces to the subject 320 along a second z-axis perpendicular to a second x/y-axis system that is tangential to a second interface zone of the subject. Generally, n analyzers 110, optionally linked to a single main controller 112, interface to n interface zones of the subject 320, where the main controller 112 is optionally and preferably electrically, mechanically, and/or communicatively linked with any and preferably all subsystems of the analyzer 110 and is used to control the analyzer 110, such as via computer hardware and associated software.

EXAMPLE II

Still referring to FIG. 13, each of the analyzers interfacing to the subject 320 optionally comprise any system of the analyzer 110. As illustrated, the first analyzer version 371, which is an example of the analyzer 110 comprises three analyzer versions, illustrated as the first spectrometer version 142, the second spectrometer version 144, and the third spectrometer version 146. As illustrated, the first spectrometer version 142, optionally in the form of a watch head, interfaces to the subject 320 along a first z-axis perpendicular to a first x/y-plane, which tangentially touches the upper arm 372 at a first interface point; the second spectrometer version 144 has the form of a watch band link and interfaces to the subject 320 along a second z-axis perpendicular to a second x/y-plane, which tangentially touches the upper arm 372 at a second interface point; and the third spectrometer version 146, optionally in the form of a watch band attachment, interfaces to the subject 320 along a third z-axis perpendicular to a third x/y-plane, which tangentially touches the upper arm 372 at a third interface point. Each of the three spectrometer versions 142, 144, 146 are optionally attached to the upper arm 146 via double-sided adhesives and are thus attached in the manner of a sticker. As illustrated, the three spectrometer versions 142, 144, 146 are attached to the upper arm 372 with a flexible band 148, such as a watch band or an elastic band. The individual spectrometer versions 142, 144, 146 are optionally connected using one or more hinge components and or rotating connectors. The individual spectrometer versions 142, 144, 146 are optionally replaceably connected to the subject along separate planes forming angles therebetween of greater than 1, 2, 5, 10, 15, 25, or 25 degrees. The hinge allows tangential interfacing of illumination zones of the respective spectrometer version along a curved surface of the subject 320. Optionally, the hinge allows for rotation of a first spectrometer unit relative to a second spectrometer unit to maintain tangential contact of the illumination zones with the subject 320 as the skin of the subject moves, such as by allowing a rotation of greater than 0.1, 0.5, 1, 2, or 5 degrees. The multiple planes of attachment of the analyzer 110 to the subject 320 allow attachment of multiple sources and/or detectors to the subject 320 along a curved skin surface of the subject 320, such as around the upper arm 372 and/or the lower arm 374, as illustrated with the second analyzer/spectrometer version 373 attached to the wrist of the subject 320, with minimal applied tissue deformation forces at each of the analyzer/subject interface zones. Reduced forces, such as an applied mass, stress, and/or strain aids precision and/or accuracy of the analyzer 110 by reducing movement of fluids within the tissue layers 340 of the subject 320, reducing changes in pathlength, and/or reducing changes in pressure induced scattering of light.

EXAMPLE III

Still referring to FIG. 13, in a first case, each of the first spectrometer version 142, second spectrometer version 144, and third spectrometer version 146 optionally contain all of the functionality of the analyzer 110. However, optionally, one or more optical sources are in one interfacing aspect of the first analyzer version 371, such as in the second spectrometer version 144, without any functional optical detectors in the second spectrometer version 144. In this case, the optical detectors are in a second interfacing aspect of the first analyzer version 371, such as in the first spectrometer version 142. For clarity of presentation and without loss of generality, a particular example is provided. In this example, the detector system 500 is positioned in the analyzer 110 in the first spectrometer version 142 along with optional illuminators of the source system 400. However, the source system also includes photon sources in the second spectrometer version 144, such as in a watch band link position. In this manner, photonic illuminators with short optical distances to the detector system 500 are positioned in the first spectrometer version 142, such as in close proximity to the detector system 500. For instance, photonic sources emitting in wavelength ranges: (1) with an optical absorbance of greater than one unit per millimeter of pathlength and/or (2) in the 1350 to 1560 nm range, such as within 25 mm of 1510, 1520, 1530, or 1540 nm are positioned near the detector system 500, such as in the same housing as the detector system 500, in the first spectrometer version 142, and/or with a radial distance between an illumination zone and a detection zone of less than 10, 8, 6, 5, 4, 3, 2, 1.5, or 1 millimeters. However, photonic sources emitting in lower absorbance regions, such as from 400 to 1350 nm and/or 1565 to 1800 and/or in regions of absorbance by skin at a level of less than one absorbance unit per millimeter of pathlength are positioned in the second spectrometer version 144, thus giving the photons a longer pathlength to the detector system 500 in the first spectrometer version 142. The longer selected pathlength, as selected by a detector element of the detector system 500, from a given source reduces a range of observed pathlengths by photons from the given source, as described supra. Further, each spectrometer version 142, 144, 146 allows an independent mean photon path entering the skin of the subject 320 to be perpendicular to the subject 320 despite the radius of curvature of the skin of the subject 320 as the differing spectrometer versions 142, 144, 146 are each positioned with an x/y-plane interface tangential to the local curvature of the skin of the subject 320, such as at different positions on a watch band equivalent. Optionally and preferably, the x/y-planes tangential to the subject 320 at local sample interface sites for the n interface points of the analyzer 110, such as the first interface location of the first spectrometer version 142, the second interface location of the second spectrometer version 144, and the third interface location of the third spectrometer version 146 are separated by greater than 5, 6, 7, 8, 9, 10, 12, 14, 16, 18, or 20 millimeters as measured along the skin surface. Hence, second photon sources for providing second wavelengths for measuring oxygen and/or scattering of light, such as from 400 to 1300 nm, are optionally placed in a second housing along a second position of the watch band while first photon sources for providing first wavelengths, such as at glucose absorbing wavelengths from 1500 to 2400 nm, are optionally placed in a first housing proximate detector elements, where the detector elements in the first housing detect photons from second, third, . . . , $n^{th}$ housings, such as along a circumferential band around a curved body part, where n is a positive integer greater than 1, 2, or 3.

EXAMPLE IV

In the first spectrometer version 371 of the analyzer 110, three sample interface zones are used, a first sample interface zone, such as the back of a watch zone where the source system 400, force system 200, and/or a first set of optics, such as in the first spectrometer version 142, interface to the subject 320; a second interface zone, such as where a second set of optics, such as in the second spectrometer version 144, interface to the subject 320; and a third interface zone, such as where a third set of optics, such as in a third spectrometer version 146, interface to the subject 320. Generally, any number n of sets of optics interface to the subject 320 to yield n sets of data on a state of the subject 320 where n is a positive integer, such as 1, 2, 3, 4, 5 or more. Optionally, the n sets of optics generate simultaneous data on a single state of the subject 320. However, each sub-set of optics in the n sets of optics are optionally configured to measure the same analyte and/or different analytes, such as one of more of percent oxygen saturation, heart rate, heart rate variability, glucose concentration, protein concentration, fat, muscle, protein concentration, albumin concentration, globulin concentration, respiration rate, an electrocardiogram, blood pressure, body temperature, environmental temperature, and acceleration of the subject 320.

Depth Resolution

Photons scatter in tissue. However, a mean photon path between an illumination zone and a detection zone has a mean/medium/average depth of penetration into the skin layers 340 and glucose is present at differing concentrations as a function of depth into the skin layers 340. A target zone of probing photons is the epidermis 344 and/or dermis 346 between the stratum corneum 342 and the subcutaneous fat 348. Targeting these well perfused tissue layers is described herein by way of non-limiting examples.

EXAMPLE I

Figure 14A:
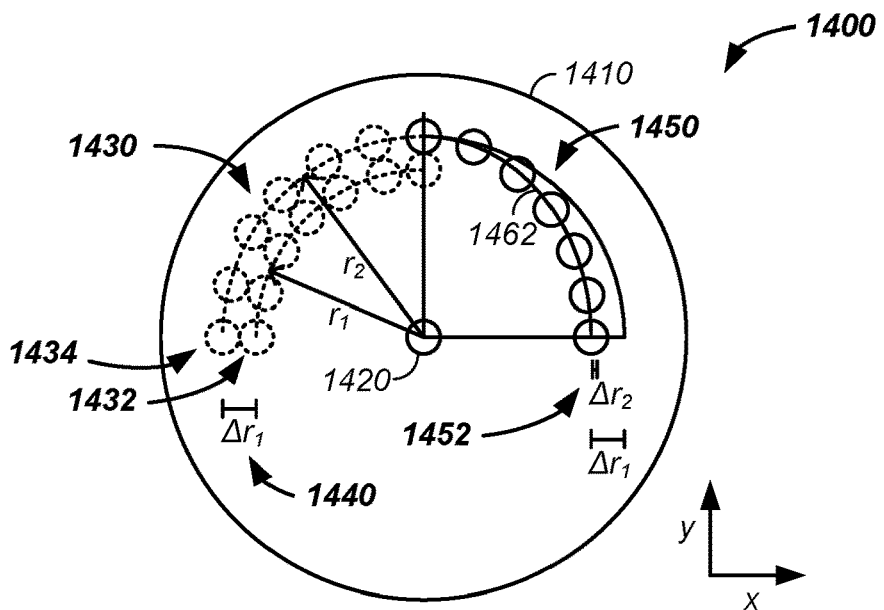
FIG. 14A illustrates spirally distributed detectors and FIG. 14B and FIG. 14C illustrate depth and radial distance resolution.

Referring now to FIG. 14A, an example of a probe tip 1400 of the source system 400 of the analyzer 110 is presented. The probe tip has a tissue contacting surface 1410 and at least one illumination zone of a set of illumination zones 1420. For clarity of presentation and without loss of generality, a single illumination zone is illustrated which is optionally and preferably one illumination zone of a plurality of illumination zones, such as where a given illumination zone is a surface area of the skin/probe tip interface illuminated by a given source, such as a given light emitting diode. More particularly, 2, 3, 4, or 5, or more, light emitting diodes/laser diodes couple to the skin, optionally via intervening optics of the photon transport system 450, to illuminate a corresponding second, third, fourth, and fifth, or more, skin/probe tip interface areas, referred to herein as illumination zones. Similarly, a given detector element optically couples, such as by the photon transport system 450 to a given surface area of the skin/probe tip interface, which is referred to as a detection zone. More particularly, 2, 3, 4, or 5, or more, detector elements, of the detector system 500, optically interface, such as through optics of the photon transport system 450 with the skin, to detect photons emitting from a corresponding second, third, fourth, and fifth, or more, skin/probe tip interface area, referred to herein as detection zones. A mean optical path for a set of photons is a mean pathway through the tissue layers 340 of the subject 320 between a given illumination zone and a given detection zone. Optionally, the probe tip 1400 is of any geometry. Optionally, illumination zones are of any pattern on the probe tip 1400. Optionally, detection zones are of any layout on the probe tip 1400.

EXAMPLE II

Figure 14B:
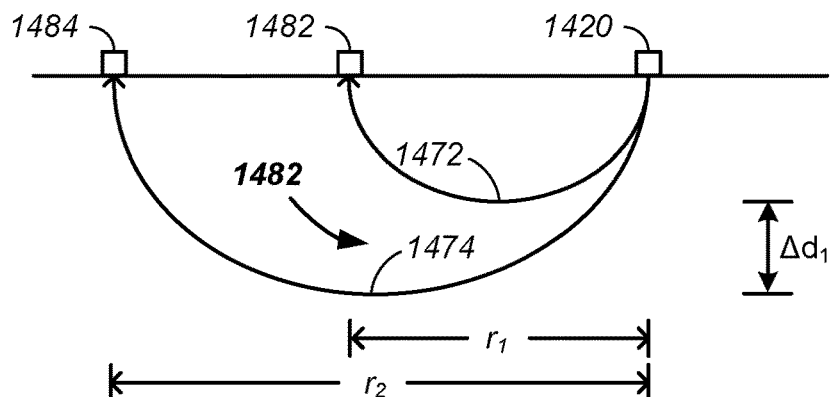

Referring still to FIG. 14A and referring now to FIG. 14B, resolution of a mean depth of penetration of probing photons between an illumination zone and rings of detectors 1430 is provided. As illustrated, a first ring of detectors 1432, coupled to a first set of detection zones, is at a first radius, $r_1$, from the illumination zone and a second ring of detectors 1434, coupled to a second set of detection zones, is at a second radius, $r_2$, from the illumination zone. For clarity of presentation and without loss of generality, the detectors and detector zones are illustrated with the same circular graphical representation herein. Further, the circular graphical representations are optionally illustrative of the ends of fiber optics coupled to corresponding detectors or sources. At close distances having an observed absorbance of less than one, the mean depth of penetration of probing photons increases with radial distance. The first and second ring of detectors 1432, 1434 are separated by a radial distance difference, $\Delta r_1$. Referring now to FIG. 14B, the first ring of detectors 1432 corresponds to a first mean optical path 1472 having a first depth of penetration into the tissue layers 340 and the second ring of detectors 1434 corresponds to a second mean optical path 1474 having a second depth of penetration into the tissue layers 340. As illustrated, for a first radial detector 1482 at the first radial distance, $r_1$, the maximum depth of the first mean optical path 1472 and the second mean optical path, for a second radial detector 1484 at a second radial distance, $r_2$, have a depth of penetration difference, $\Delta d_1$. Notably, the second ring of detectors 1434 is spatially positioned at a closest linear distance, the line passing through an illumination zone of the set of illumination zones 1420, to the first ring of detectors 1432. Thus, the best resolution of depth is the depth of penetration difference, $\Delta d_1$, corresponding to a first range of tissue thicknesses 1482. However, in many cases, as the thicknesses of the epidermis 344 and dermis 346 changes with applied pressure, force, hydration, spatial orientation, movement, and/or changes in blood constituent concentration, the targeted dermal layers are not resolved using the best resolution of concentric detector rings with a difference in radial distance, $\Delta r_1$, to the illumination zone corresponding to the resolved depth, $\Delta d_1$.

EXAMPLE III

Figure 14C:
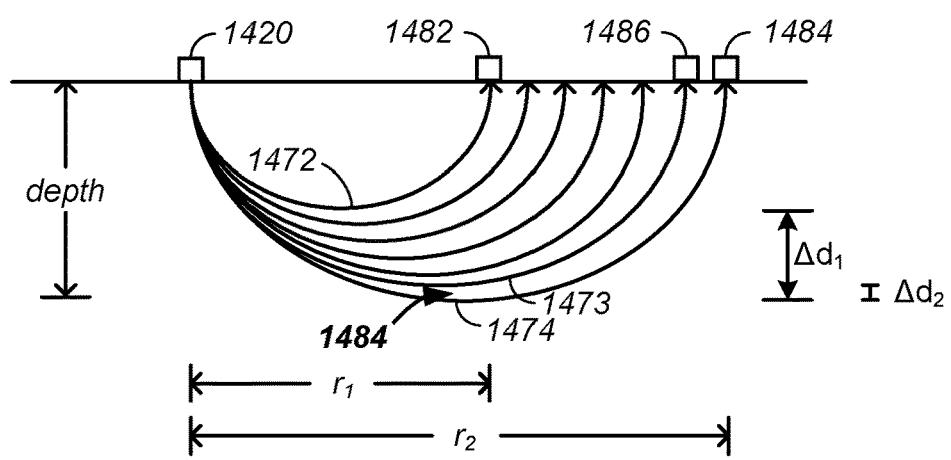

Referring still to FIG. 14A and FIG. 14B and referring now to FIG. 14C, a comparison of resolution of a mean depth of penetration of probing photons between an illumination zone and rings of detectors 1430 and arcs of detectors 1450 is provided. Herein, an arc of detectors is a set of detectors along a curved path of multiple radial distances from an illumination zone. The arced path is not an arc of a circle. Rather, the arced path is along a spiral and/or curve covering a range of radial distances from an illumination zone. As illustrated an arc of detectors 1450, along an optional arc layout 1462, starts at the first radial distance, $r_1$, of the first ring of detectors 1432 and ends at the second radial distance, $r_2$, of the second ring of detectors. While the first and second ring of detectors have a first linear radial distance difference, $r_1$, that is based on the size of the detector element housing, fiber optic, and/or detection zone, the illustrated arc of detectors 1450 has a second linear radial distance difference, $r_2$, that is smaller than, $r_1$. Particularly, with the seven illustrated detectors in the arc of detectors, the second linear radial distance, $r_2$, is one-seventh that of the first radial distance, Generally, the difference in radial distance is better than ½, ⅓, ¼, ⅕, . . . , 1/n that of the spatially constrained concentric rings of detectors for n detector elements in an arc bounded by the first and second radial distances, $r_1$ and $r_2$, of the concentric rings of detectors, where n is a positive integer of greater than 2, 3, 4, 5, 10, or 20. Comparing now the first and second mean depths of penetrations 1472, 1474 for the first and second ring of detectors 1432, 1434 and the first and second detector 1482, 1484, with the range of mean depths of penetrations in FIG. 14C corresponding to the individual illumination zones, of the set of illumination zones 1420, to detection zones of detector elements in the ring of detector elements 1450, the enhanced resolution is illustratively obvious. Particularly, the above described first resolved depth, $\Delta d_1$, corresponding to the first and second ring of detectors 1432, 1434 is seven times larger than a second resolved depth, $\Delta d_2$, between a third mean path 1437 and a fourth mean path 1474 corresponding to the second radial detector 1484 and a closest intermediate radial detector 1486, two detector elements in the arc of detectors 1450. Particularly, a second range of tissue thicknesses 1484 is thinner than the first range of tissue thicknesses 1482, described supra. Generally, the difference in resolved tissue depth is better than ½, ⅓, ¼, ⅕, . . . , 1/n that of the spatially constrained concentric rings of detectors for n detector elements in an arc bounded by the first and second radial distances, $r_1$ and $r_2$, of the concentric rings of detectors, where n is a positive integer of greater than 2, 3, 4, 5, 10, or 20. Thus, arcs of detection zones corresponding to arcs of detectors and/or coupling optics, such as fiber optics, spanning a range of radial distances from an illumination zone yield an enhanced resolution of tissue depth. Further, as described supra, dynamic selection of signals from detector elements radially inward from an outwardly positioned detector element observing a disproportionate increase in a fat band absorbance, which is an example of a spectroscopic marker, from the subcutaneous fat 348, at a greater depth than the targeted dermis 346, yields the largest radial distance observing the desired/targeted dermal layers. Further, as the epidermis 344 and dermis 346 change in thickness, such as due to subject movement, orientation, and/or hydration, and/or changes in body chemistry, the range of resolved depths of penetration corresponding to the range of radial distances between the illumination zone and individual detection zones allows dynamic selection of source-to-detector distances currently probing the desired dermal layers, such as the epidermis 344 and the dermis 346.

Depth/Location Selection

Referring now to FIGS. 15A, 15B, 15C, 15D, 16A, 16B, 16C, 16D, and 17, a method and apparatus are described for selecting, as a function of wavelength, illumination zone-to-detection zone distances yielding a common and/or overlapping depth of sampling and/or position of sampling. In the examples provided, for clarity of presentation and without loss of generality, notation of a first, second, third, . . . , $n^{th}$ source and/or detector is used where the $n^{th}$ source/detector in one example is optionally distinct from the $n^{th}$ source/detector in another example. Further, it is understood that skin layers are not homogenous and that variations occur from tissue voxel to tissue voxel. However, sampling a common depth and location aids in measuring a common sample state within the non-homogenous tissue layers, especially when used in conjunction with one or more of: a larger illumination zone, a larger detection zone, sample movement relative to the analyzer, and/or analyzer movement relative to the sample.

EXAMPLE I

Referring now to FIG. 15A, FIG. 15B, FIG. 15C, and FIG. 15D in this first example, a common depth selection system 1500 and method of use thereof is described.

Figure 15A:
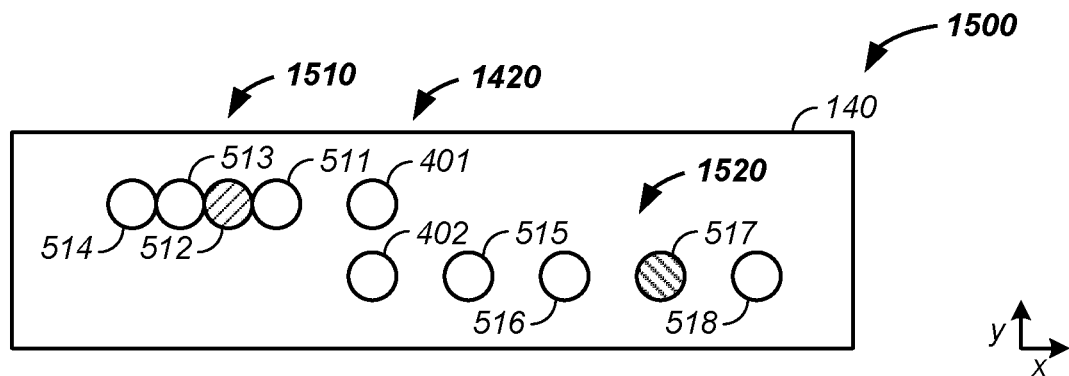
FIG. 15A, FIG. 15B, FIG. 15C, and FIG. 15D illustrate depth selection from various angles in two separate units.

Referring now to FIG. 15A. The spectrometer includes a first source 401/source element, illuminating a first illumination zone of the set of illumination zones 1420. Light from the first illumination zone is detected by a set of detectors 1510, such as a first detector 511 detecting photons at a first detection zone, a second detector 512 detecting photons at a second detection zone, a third detector 513 detecting photons at a third detection zone, and/or a fourth detector 514 detecting photons at a fourth detection zone. Herein, the sources and detectors are illustrated at the skin surface for clarity of presentation and without loss of generality. However, it should be understood that the actual source and/or detector elements, are optionally positioned anywhere, and are optionally and preferably optically coupled to their respective source zone/detection zone via air and/or one or more optics. For instance, a source optionally uses a fiber optic, or any optic, to deliver light from the source to the outer skin surface 330. Similarly, a detector optionally uses any optic to deliver a portion of the photons emitting from a detection zone, optically visible to the detector, to the detector element.

Figure 15B:
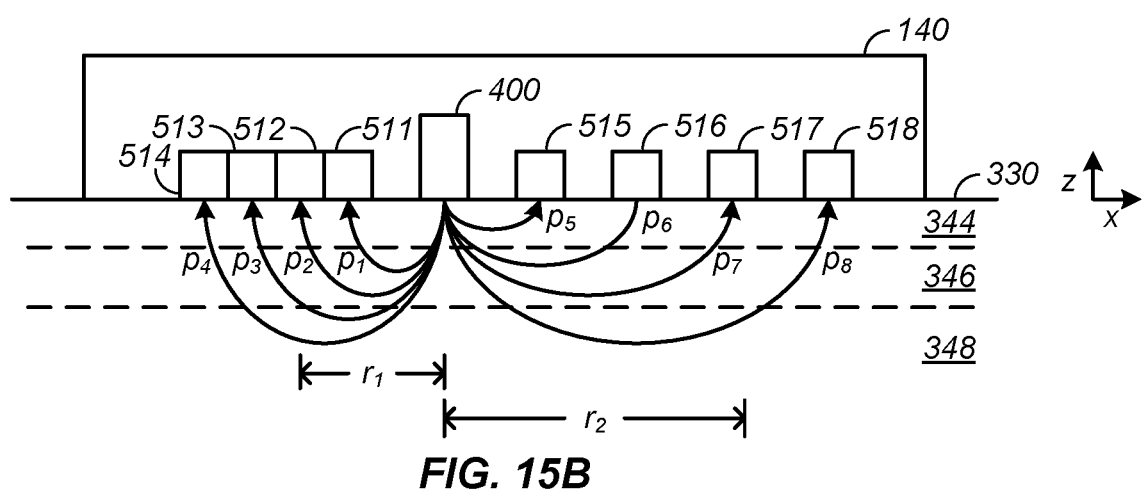

Referring still to FIG. 15A and referring now to FIG. 15B, depths of penetration of photons passing from the set of illumination zones 1420 to the set of detectors 1520 is illustrated. As illustrated, photons have a first mean path, $p_1$, from the first illumination zone associated with and/or optically linked to the first source 401 and to a first detection zone associated with and/or optically linked to the first detector 511. Similarly, as illustrated, photons have a second mean path, $p_2$, from the first illumination zone associated with and/or optically linked to the second source 402 and to a second detection zone associated with and/or optically linked to the second detector 512. Similarly, a third mean path, $p_3$, and fourth mean path, $p_4$, link the third detector 513 and fourth detector 514 to the first source 401. It should be understood that the actual mean optical paths are not clear arcs as illustrated and the mean paths rather illustrate the point that differing illumination zone-to-detector zone distances have differing coupling mean pathways and/or the pathways probed differing sample layers at different weights. As illustrated, the second mean path, $p_2$, is the longest path in the dermis layer 346 that does not substantially pass through the subcutaneous fat layer 348, which is a first selection metric, which is an example of a selection metric. In this example, the second mean path, $p_2$, is a first selected path based upon the selection metric. Selection metrics are optionally generated using one or more readings related to absorbance of fat, water, and/or protein. It should be understood that the first source 401 is illustrated at a first illumination zone only for clarity of presentation and the first source is optionally and preferably embedded into the analyzer 110 and coupled to the illustrated illumination zone with or without a coupling optic and that this general presentation approach holds for each source and similarly holds for each detector where a given detector is illustrated at a detection zone where optionally and preferably the given detector is configured to view the detection zone with or without an intervening optic.

Referring still to FIG. 15A and FIG. 15B, depths of penetration of photons passing from the set of illumination zones 1420 to the set of detectors 1520 is further described for a second wavelength range, where photons from the first source 401 have a first distribution of intensity as a function of wavelength and a first mean wavelength and photons from a second source 402 have a second distribution of intensity as a function of wavelength and a second mean wavelength differing from the first mean wavelength by greater than 1, 2, 5, 10, 20, 50, or 100 nm. Photons from the second source 402 interact with tissue differently from the photons from the first source 401, in terms of absorbance and scattering, which results in differing total pathlengths and sample pathlength in tissue layers, such as the epidermis 344, dermis 346, and/or subcutaneous fat 348. As illustrated, a second set of wavelengths, from the second source 402, reaching the surface of the skin 330 have longer observed mean pathlengths than a first set of wavelengths, from the first source 401, reaching the outer skin surface 330 or surface of the skin. For instance, the second set of wavelengths cover a wavelength range with lower overall absorbance of the sample constituents, such as a lower water absorbance, than the first set of wavelengths. As above, photons from the second source 402 have a fifth mean optical path, $p_5$/fifth path/fifth mean path; a sixth mean path, $p_6$; a seventh mean path, $p_7$; and an eighth mean path, $p_8$, to a fifth, sixth, seventh, and eighth detection zone observed by a fifth detector 515, a sixth detector 516, a seventh detector 517, and an eighth detector 518, respectively. Generally, any number of sources, m; any number of detectors, n; and/or any number of radial distances, r, are optionally used, where m and n are positive integers and r is a distance of greater than 0.01, 0.1, 0.5, 1, 1.5, 2, 3, 4, 5, or 10 millimeters.

Still referring to FIG. 15A and FIG. 15B, using the same criteria of the longest observed path in the dermis layer 346 that does not substantially pass through the subcutaneous fat layer 348, the seventh path, $p_7$, is a second selected path based upon the first selection metric. The first selected path, $p_2$, and the second selected path, $p_7$, are both weighted to a common sample depth, the dermis 346. Hence, (1) the first source 401 coupled to the second detector 512 and (2) the second source 402 coupled to the seventh detector 517 each have weighted sampling to a common sample, the dermis 346. In stark contrast, at a radial distance, such as observed at the first detector 511 and fifth detector 515, the mean photons sample differing samples; the first source 401 dominantly sampling both the epidermis 344 and dermis 348, as illustrated by the first path, $p_1$, and the second source 402 dominantly sampling the epidermis 344, as illustrated by the fifth path, $p_5$.

Figure 15C:
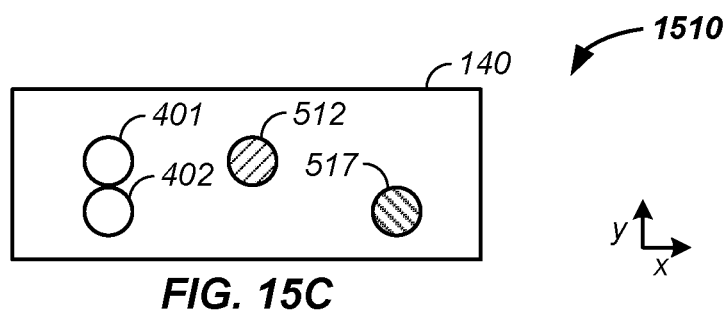
Figure 15D:
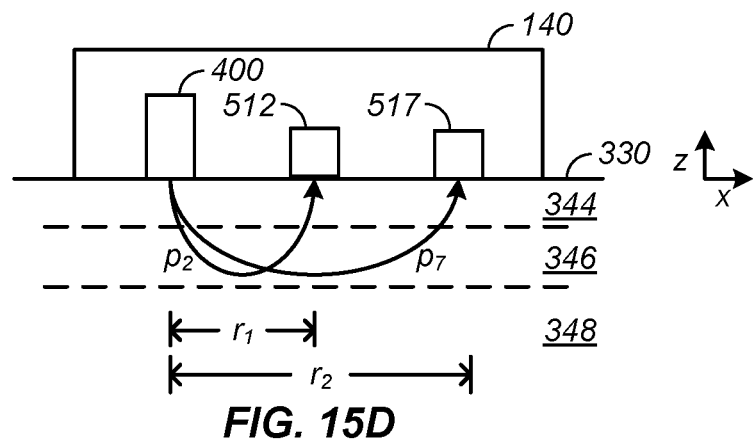

Referring now to FIG. 15C, the chosen radial separations of the sources and detectors, such as chosen in the preceding paragraph of this first example, are illustrated in an optional second probe configuration 1510. Particularly, (1) a first selected radial distance, $r_1$, between the first source 401 and the selected second detector 512 is maintained and (2) a second radial distance, $r_2$, between the second source 402 and the selected seventh detector 517 is maintained without the need of the additional detector elements. Thus, for a static sample, the benefits of the common depth selection system 1500 are maintained in the second probe configuration 1510.

EXAMPLE II

Referring now to FIG. 16A, FIG. 16B, FIG. 16C, and FIG. 16D in this second example, a common sample position selection system 1600 and method of use thereof is described, where the common sample position is optionally and preferably at the common depth, such as the dermis, described supra.

Figure 16A:
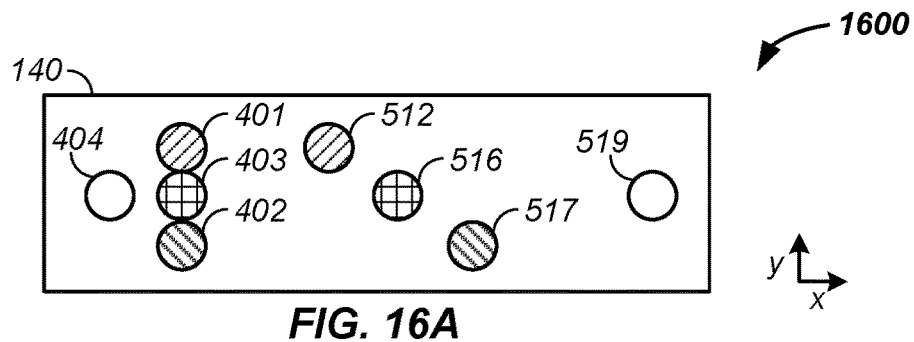
FIG. 16A, FIG. 16B, FIG. 16C, and FIG. 16D illustrate tissue sample position selection.
Figure 16B:
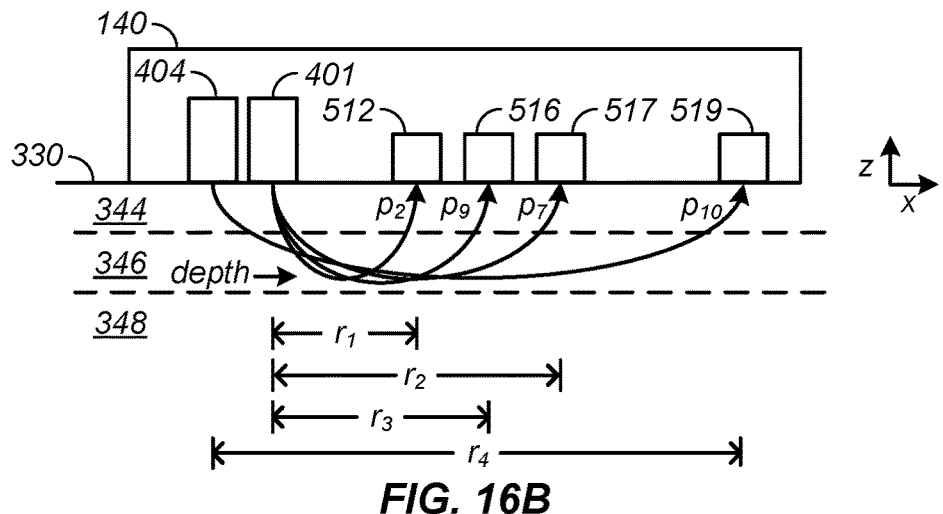

Referring still to FIG. 16A and FIG. 16B, the common sample position system 1600 is first described through an illustrated addition of two additional wavelength ranges to the common depth selection system 1500, described supra, where the resulting four wavelength ranges have four distinct mean wavelengths reaching the detector and where each of the four distinct mean wavelengths are separated from each other by at least 10 nm. Particularly, the separation of the first source 401 from the second detector 512 by the first radial distance, $r_1$, is maintained from the prior example as is the separation of the second source 402 from the seventh detector 517 by the second radial distance, $r_2$. Added to the illustration is a separation of the third source 403 from the sixth detector 516 by a third radial distance, $r_3$, and a separation of a fourth source 404 from a ninth detector 519 by a fourth radial distance, $r_4$. Notably, all of the illustrated source-to-detector distances are selected, such as by the method of the first example and/or through use of a metric, such as a measure of water, protein, and/or fat absorbance, to sample a common depth, which as illustrated is the dermis 346. An apparatus setting each of the four wavelength ranges to a same mean lateral x-position and/or y-position is described, infra.

Figure 16C:
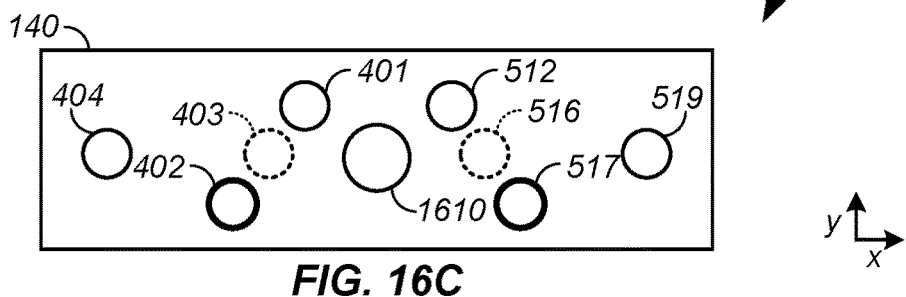
Figure 16D:
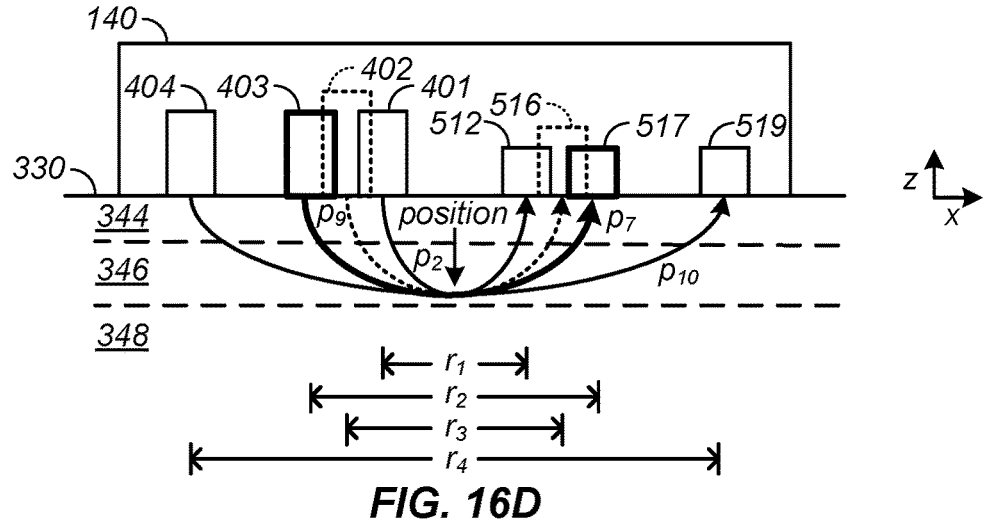

Referring now to FIG. 16C and FIG. 16D, the four source-to-detector distances, described supra, selected to sample a common depth, such as the dermis, are positioned in a probe face to yield a common lateral position at depth within the tissue or a common central zone 1610 at the surface. Particularly, a mean position between each of the source-to-detector positions is overlaid on at a common x-axis, as illustrated, and/or a common y-axis position to within less than 2, 1, 0.5, 0.4, 0.3, 0.2, or 0.1 mm.

Referring now to FIGS. 15(A-D) and FIGS. 16(A-D), while skin is not homogeneous, overlapping the photonic pathways of a set of differing wavelengths detected by a set of detectors, in terms of a common depth and/or a common position, yields a higher probability of sampling a common tissue state.

EXAMPLE III

Figure 17:
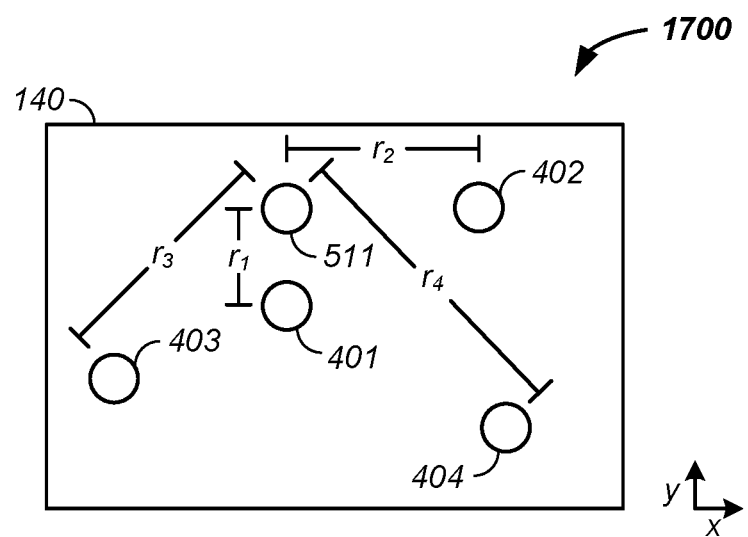
FIG. 17 illustrates a common depth and common depth analyzer probe tip.

Referring now to FIG. 17, in this third example, a common depth selection and common detector system 1700 and method of use thereof is described.

Still referring to FIG. 17, generally, different wavelengths of light, in the range of 1100 to 2500 nm, have different mean depths of penetration into skin due to skin having a large range of absorbance and/or a large range of scattering as a function of wavelength. For instance, first photons at a first wavelength where the skin absorbs heavily, such as at and/or near a peak of the water absorbance bands 710, at 1450 nm, and/or at 1900 nm, have a shallow maximum mean depth of penetration into the skin layers, such as only penetrating into the epidermis 344. Similarly, second photons at wavelengths having a lower absorbance, such as on a shoulder of the water absorbance bands 710, have a mean detected photonic path that penetrates deeper into the skin, such as into the dermis 346. Again similarly, third photons having wavelengths at a still lower absorbance, such as at and/or near a valley of the water absorbance bands 710, have a mean detected photonic path that penetrates still deeper into the skin, such as into the subcutaneous fat 348. Hence, traditional systems sampling different wavelength ranges sample different mean sample depths.

Generally, a magnitude of absorbance of the skin is inversely related to a maximum mean depth of penetration of detected photons into the skin and water absorbance, optionally modified by scattering, dominates an overall magnitude of absorbance of the skin due to waters high absorbance in the range of 1100 to 2500 nm relative to other skin constituents.

As a result of sampling differing sample depths, errors are introduced into traditional analyzers, such as a noninvasive glucose concentration analyzer, as the skin layers 340 differ in both chemical and physical makeup and hence the wavelengths actually probe different samples. Here, a system of sampling a common skin layer is described, where optionally and preferably signals with differing illumination zone-to-detector zone distances are measured with a common detection zone optically linked to a detection system, such as a detector and/or a detector optically coupled to the common detection zone with one or more optics.

Referring again to FIG. 17, for clarity of presentation and without loss of generality, a specific case of a range of wavelengths sampling a common skin layer is described. Particularly, in this case the first source 401 comprises a higher relative sample absorbance, such as within 10, 20, 30, 40, 50, 75, or 100 nm of a peak water absorbance at 1450 or 1900 nm and a first detected signal of photons from the first source 401 is dominated by a water signal at a first radial distance, $r_1$, to the first detector 511, where the first radial distance is set at a distance yielding a maximum mean photonic path in the dermis 346. Further, in this case the second source 402 comprises a mid-range sample absorbance, such as within 10, 20, 30, 40, or 50 nm of a mid-point absorbance of the peak water absorbance bands, such as at 1410, 1520, 1870, 2020, or 2380 nm, where the second detected signal of photons from the second source 402 is still dominated by a water signal at a second radial distance, $r_2$, but, the second wavelength range also samples another sample constituent, such as glucose, while still yielding a maximum mean photonic path in the dermis 346. Notably, to sample the same depth as the first illumination zone-to-detection distance, while being as a second wavelength of lower overall absorbance, the second radial distance is larger than the first radial distance. Still further, in this case the third source 403 comprises a still lower sample absorbance, such as within 10, 20, 30, or 40 nm of a first quartile point of the peak water absorbance bands, such as at 1380, 1550, 1850, 2090, or 2350 nm, where the third detected signal of photons from the third source 403 is still dominated by a water signal at a third radial distance, $r_3$, but, the third wavelength range also samples another sample constituent, such as protein, while still yielding a maximum mean photonic path in the dermis 346 by having the third radial distance be longer than the second radial distance, which is in turn larger than the first radial distance. Yet still further, in this case the fourth source 404 comprises the still lower sample absorbance, such as within 10, 20, 30, or 40 nm of the first quartile point of the peak water absorbance bands, such as at 1380, 1550, 1850, 2090, or 2350 nm, where the fourth detected signal of photons from the fourth source 404 is still dominated by a water signal at a fourth radial distance, $r_4$, but, the fourth wavelength range also samples another sample constituent, such as the subcutaneous fat 348, by having the fourth radial distance be further from detection zone relative to the third radial distance. Stated again, although the third source 413 emits third detected photons at a higher water absorbance wavelength/value relative to a lower water absorbance/value in a range of fourth detected photons, the maximum mean depth of the fourth photons penetrates further into the sample, such as the subcutaneous fat 348 relative to the dermis 346 probed by the third photons, due to the larger radial distance of the fourth radial distance relative to the third radial distance. Optionally, the third radial distance is configured to measure protein, such as at a wavelength with 5, or 10 nanometers of 1690 nm. Optionally, the fourth radial distance is configured to measure subcutaneous fat, such as at a wavelength with 5 or 10 nanometers of 1710 nm.

Figure 7A:
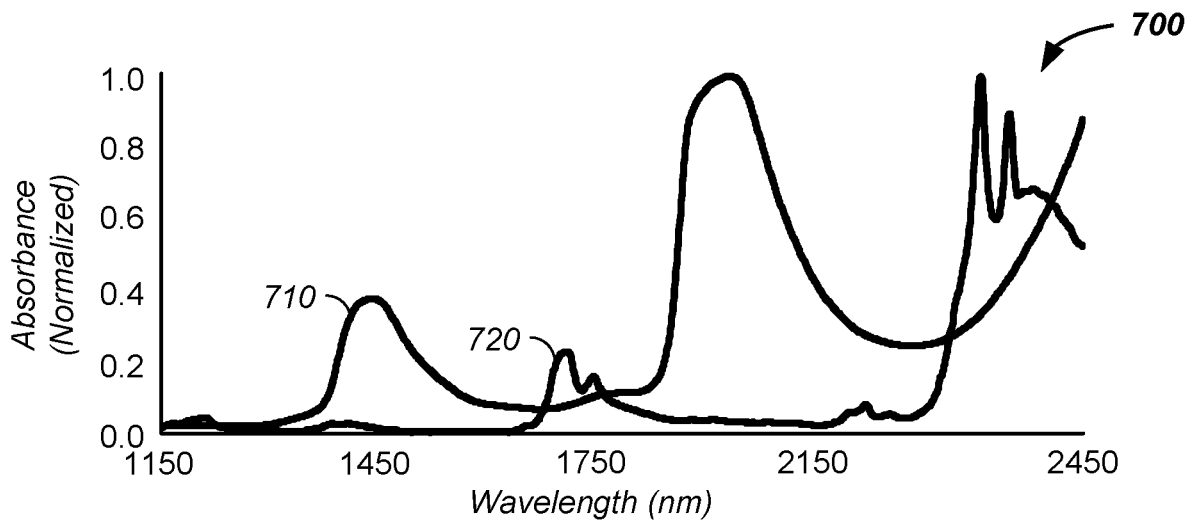
FIG. 7A illustrates absorbance of skin constituents.
Figure 7B:
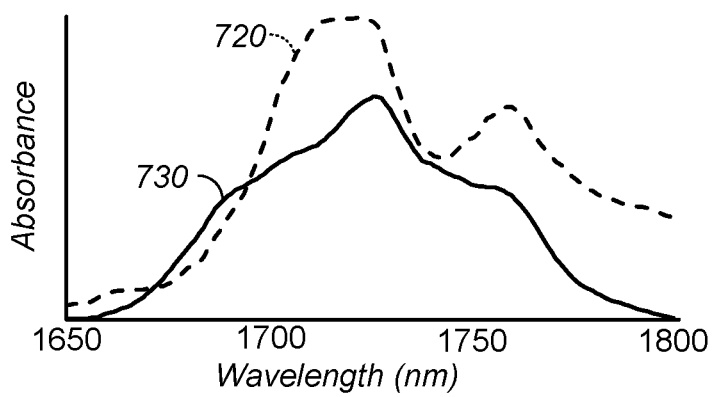
FIG. 7B illustrates fat and protein absorbance.
Figure 7C:
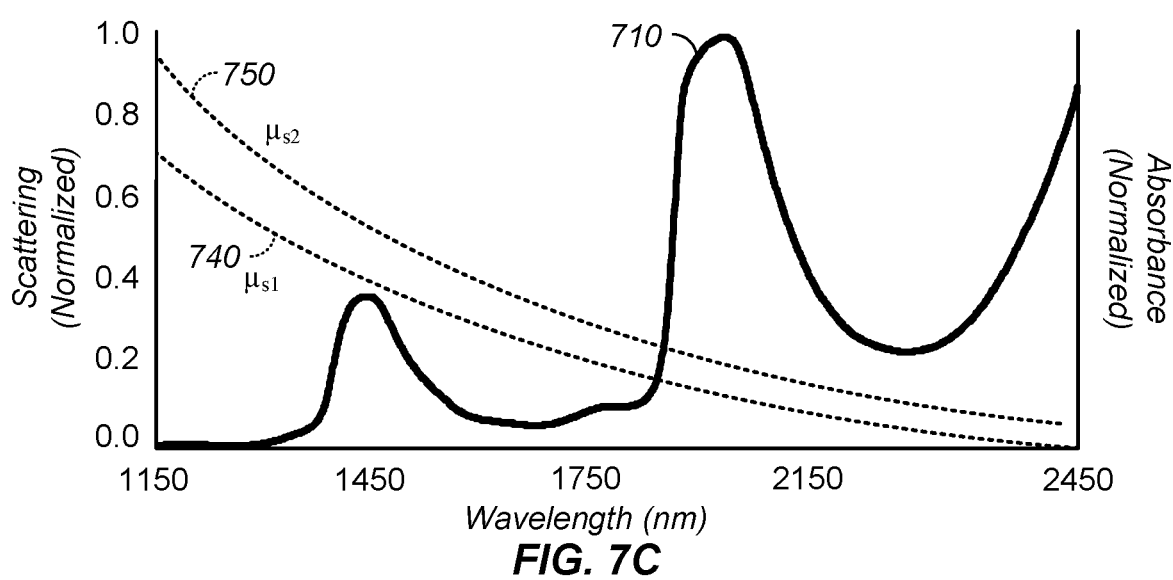
FIG. 7C illustrates scattering.

Still referring to FIG. 7A, optionally, a common detection zone linked to a common detector system is used to sample light from the first, second, third, and fourth radial distances from the first source 401, the second source 402, the third source 403, and the fourth source 404, respectively. Generally, targeting skin layers 340 is demonstrated for each of a set of range of wavelength ranges, where each member of the set of wavelength ranges comprising a source-to-detector distance set by prior analysis, skin absorbance, water absorbance, and/or scattering. Notably, enhanced precision of depth targeting is achieved by measuring a range of illumination zone-to-detection zone distances. In this example, the higher relative absorbance is at least 20, 30, 40, 50, 75, or 100 percent higher than the mid-range absorbance. In this example mid-range absorbance is at least 20, 30, 40, 50, 75, or 100 percent higher than the lower quartile absorbance. In this example, the second radial distance is at least 0.2, 0.3, 0.4, 0.5, 0.75, or 1 mm larger than the first radial distance; the third radial distance is at least 0.2, 0.3, 0.4, 0.5, 0.75, or 1 mm larger than the second radial distance; and/or the third radial distance is at least 0.2, 0.3, 0.4, 0.5, 0.75, or 1 mm larger than the fourth radial distance.

Optionally and preferably, the sources are light emitting diodes, laser diodes, and/or provide a narrow band of light through use of a long pass filter, a short pass filter, a bandpass filter, and/or an optical filter. Generally, a given optional source system intended to illuminate a given wavelength region may provide additional photons at other regions of higher water absorbance, where the water absorbance blocks the additional photons. Generally, a given source intended to illuminate a given wavelength range, in the 1100 to 2500 nm wavelength region, does not provide more than 20, 10, 5, or 0 percent of the light in a lower absorbing region. For instance, a source intended to provide photons for analysis of fat at 1710 nm may provide photons from 1700 to 1720 nm, where photons at 1900 to 2000 nm are optionally provided as they are absorbed by water in the skin, and where photons at 1500 to 1650 nm are provided only at low intensity or are optically blocked as the water of the skin allows more of the photons in the 1500 to 1650 nm region to reach the detector and are thus avoided for analysis of the fat. Similarly, each intend wavelength, for analytes such as water, protein, and glucose, have similar source requirements for a common detector system. In an optional case where one or more detector systems has blocking optics for different wavelengths, the limitations on the source systems described herein is removed.

Acousto-Optic Analyzer vs. (1) UPI and (2) an AOTF

An applied force-optic analyzer is described herein. Optionally and preferably, the applied force results in a mechanical disturbance of the tissue resulting in a force being applied to the sample. However, in a sub-case of the applied force-optic analyzer, the applied force comprises an acoustic force yielding an acousto-optic analyzer. Notably, in the sub-case of the applied force-optic analyzer being an acousto-optic analyzer, as used herein an acousto-optic analyzer starkly contrasts with both: (1) an ultrasonic photoacoustic imaging (UPI) system and (2) an acousto-optic tunable filter (AOTF) spectrometer, as described infra.

Acousto-Optic Analyzer

As described, an acousto-optic analyzer (AOA) introduces an acoustic vibration wave to the sample to impact the state of the sample, such as tissue, and the state of the sample is measured using an optical probe.

Photoacoustic Imaging

In stark contrast, according to Wikipedia, ultrasonic photoacoustic imaging, also referred to as (UPI), photoacoustic imaging (PI), and/or optoacoustic imaging, delivers non-ionizing laser pulses to biological tissue, which results in absorbed energy and resultant heat in the form of transient thermoelastic expansions detected as wideband megaHertz ultrasonic emissions detected by ultrasonic transducers. The detected signals are used to produce images. As optical absorbance relationships exist with physiological properties, such as hemoglobin concentration and oxygen saturation, the detected pressure waves may be used to determine hemoglobin and oxygen concentration.

Hence, an acousto-optic analyzer starkly contrasts with photoacoustic imaging. Stated again, while the acousto-optic analyzer described herein may induce a heat wave like in photoacoustic imaging, in photoacoustic imaging the sound wave is detected whereas photons, from an external source, are detected in the acousto-optic analyzer described are detected after interacting with the sample being displaced/heated/disturbed by the sound wave.

Acousto-Optic Tunable Filter

According to Wikipedia, an acousto-optic tunable filter (AOTF), diffracts light based on an acoustic frequency. By tuning the frequency of the acoustic wave, the desired wavelength of the optical wave can be diffracted acousto-optically.

Hence, an acousto-optic analyzer (AOA) starkly contrasts with an acousto-optic tunable filter (AOTF) as, while the input sound wave of the AOA may diffract light, the separation of the input light is not the primary use of the sound wave. Indeed, a narrow-band light emitting diode (LED) is optionally used in conjunction with a broadband detector in the acousto-optic analyzer making any separation of the narrow band light source pointless. Further, in the AOA, the sound wave is used to change the state of the biological sample itself, whereas in the AOTF the sound wave is introduced to a birefringent crystal in a wavelength separation module of the spectrometer and is not introduced into the sample.

Still yet another embodiment includes any combination and/or permutation of any of the elements described herein.

The main controller, a localized communication apparatus, and/or a system for communication of information optionally comprises one or more subsystems stored on a client. The client is a computing platform configured to act as a client device or other computing device, such as a computer, personal computer, a digital media device, and/or a personal digital assistant. The client comprises a processor that is optionally coupled to one or more internal or external input device, such as a mouse, a keyboard, a display device, a voice recognition system, a motion recognition system, or the like. The processor is also communicatively coupled to an output device, such as a display screen or data link to display or send data and/or processed information, respectively. In one embodiment, the communication apparatus is the processor. In another embodiment, the communication apparatus is a set of instructions stored in memory that is carried out by the processor.

The client includes a computer-readable storage medium, such as memory. The memory includes, but is not limited to, an electronic, optical, magnetic, or another storage or transmission data storage medium capable of coupling to a processor, such as a processor in communication with a touch-sensitive input device linked to computer-readable instructions. Other examples of suitable media include, for example, a flash drive, a CD-ROM, read only memory (ROM), random access memory (RAM), an application-specific integrated circuit (ASIC), a DVD, magnetic disk, an optical disk, and/or a memory chip. The processor executes a set of computer-executable program code instructions stored in the memory. The instructions may comprise code from any computer-programming language, including, for example, C originally of Bell Laboratories, C++, C#, Visual Basic® (Microsoft, Redmond, Wash.), Matlab® (MathWorks, Natick, Mass.), Java® (Oracle Corporation, Redwood City, Calif.), and JavaScript® (Oracle Corporation, Redwood City, Calif.).

Herein, any number, such as 1, 2, 3, 4, 5, is optionally more than the number, less than the number, or within 1, 2, 5, 10, 20, or 50 percent of the number.

Herein, an element and/or object is optionally manually and/or mechanically moved, such as along a guiding element, with a motor, and/or under control of the main controller.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method for measuring photonic output from skin of a person for use in a noninvasive analyte determination system, comprising the steps of:
providing an analyzer, comprising:
a first source system, a second source system, a third source system, and a detector system all at least partially embedded into a probe housing;
a first illumination zone optically coupled to said first source system, a second illumination zone optically coupled to said second source system, and a third illumination zone optically coupled to said third source system;
a common detection zone optically coupled to said first detector system, said first illumination zone separated from said common detection zone by a first radial distance, said second illumination zone separated from said common detection zone by a second radial distance, and said third illumination zone separated from said common detection zone by a third radial distance, said third radial distance greater than said second radial distance, and said second radial distance greater than said first radial distance; and
respectively detecting, from the skin of the person, a first photonic signal, a second photonic signal, and a third photonic signal from said first source system, said second source system, and said third source system as a function of time, said first photonic signal comprising a first absorbance-to-first radial distance ratio at least ten percent greater than a second absorbance-to-second radial distance ratio of said second photonic signal, said second absorbance-to-second radial distance ratio of said second photonic signal at least ten percent greater than a third absorbance-to-second radial distance ratio of said third photonic signal.

2. The method of claim 1, further comprising the steps of:
said first source system illuminating said first illumination zone with first photons in a range of 1390 to 1480 nm without illuminating in a range of 1000 to 1200 nm and without illuminating in a range of 1600 to 1900 nm;
said second source system illuminating said second illumination zone with second photons in a range of 1490 to 1590 nm without illuminating in a range of 1650 to 1750 nm; and
said third source system illuminating said third illumination zone with third photons in a range of 1650 to 1800 nm without illuminating in a range of 1100 to 1300 nm and without illuminating in a range of 1500 to 1550 nm.

3. The method of claim 2, further comprising the steps of:
the first photons laterally traversing said first radial distance, said first radial distance comprising less than one millimeter;
the second photons laterally traversing said second radial distance, said second radial distance at least twenty percent greater than said first radial distance; and
the third photons laterally traversing said third radial distance, said third radial distance at least twenty percent greater than said second radial distance.

4. The method of claim 1, further comprising the steps of:
said first source system illuminating said first illumination zone with first photons in a first wavelength range;

said second source system illuminating said second illumination zone with second photons in a second wavelength range;

said third source system illuminating said third illumination zone with third photons in a third wavelength range, said first wavelength range not overlapping any of said second wavelength range and said third wavelength range, said second wavelength range not overlapping said third wavelength range.

5. The method of claim 1, further comprising the step of:
a transducer, attached to said probe housing, vibrating with a frequency in a range of five to sixty Hertz.

6. The method of claim 1, further comprising the step of:
a transducer providing a ping of energy from said probe housing into the skin under control of a processor of said analyzer.

7. The method of claim 6, further comprising the step of:
said ping of energy temporarily moving a skin layer boundary between a dermis layer of the skin and a subcutaneous fat layer of the skin.

8. The method of claim 6, further comprising the step of:
detecting a change in signal using said first detector signal resultant from said ping of energy.

9. The method of claim 7, further comprising the step of:
said processor wirelessly transmitting data from said analyzer.

10. The method of claim 1, further comprising the step of:
temporarily affixing said probe housing to the skin with a double sided adhesive.

11. The method of claim 1, further comprising the step of:
sampling a first maximum mean depth, a second maximum mean depth, and a third maximum mean depth of penetration into the skin of the person, respectively, with said first source system, said second source system, and said third source system, said first maximum mean depth, said second maximum mean depth, and said third maximum mean depth of penetration within a depth range of one millimeter.

12. The method of claim 1, further comprising the step of:
sampling a maximum mean depth range of penetration into the dermis of the skin of the person, respectively, with said first source system, said second source system, and said third source system.

13. An apparatus for measuring photonic output from skin of a person for use in a noninvasive analyte determination system, comprising:
an analyzer, comprising:
a first source system, a second source system, a third source system, and a detector system all at least partially embedded into an probe housing;
a first illumination zone optically coupled to said first source system, a second illumination zone optically coupled to said second source system, and a third illumination zone optically coupled to said third source system;
a common detection zone optically coupled to said first detector system, said first illumination zone separated from said common detection zone by a first radial distance, said second illumination zone separated from said common detection zone by a second radial distance, and said third illumination zone separated from said common detection zone by a third radial distance, said third radial distance greater than said second radial distance, said second radial distance greater than said first radial distance; and
said first detector system configured to detect a first photonic signal, a second photonic signal, and a third photonic signal, respectively, from said first source system, said second source system, and said third source system as a function of time, said first photonic signal comprising a first diode configured to emit first photons with a first absorbance-to-first radial distance ratio at least ten percent greater than a second absorbance-to-second radial distance ratio of the second photonic signal from a second diode configured to emit second photons, said second absorbance-to-second radial distance ratio of the second photonic signal at least ten percent greater than a third absorbance-to-second radial distance ratio of the third photonic signal from a third diode.

14. The apparatus of claim 13, further comprising:
said first source system comprising said first diode, said second source system comprising said second diode, and said third source system comprising said third source diode, said second diode configured to emit photons in a range of 1500 to 1550 nm.

15. The apparatus of claim 14, said third diode further comprising:
a laser diode configured to emit light in a range of 1650 to 1750 nm.

16. The apparatus of claim 13, further comprising:
a transducer at least partially embedded in said probe housing, said transducer configured to vibrate at a frequency in a range of five to sixty Hertz.

17. The apparatus of claim 13, said first detection zone coupled to a single fiber optic comprising a length of less than five millimeters.

* * * * *